(12) United States Patent
Flower et al.

(10) Patent No.: US 10,413,422 B2
(45) Date of Patent: Sep. 17, 2019

(54) INTERVERTEBRAL IMPLANT

(71) Applicant: DePuy Synthes Products, Inc., Raynham, MA (US)

(72) Inventors: Robert Flower, Sun City, CA (US); Christopher Warren, Aliso Viejo, CA (US); Fausto Olmos, Laguna Niguel, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/347,012

(22) Filed: Nov. 9, 2016

(65) Prior Publication Data
US 2017/0143507 A1 May 25, 2017

Related U.S. Application Data

(63) Continuation of application No. 13/789,507, filed on Mar. 7, 2013, now Pat. No. 9,522,070.

(51) Int. Cl.
*A61F 2/44* (2006.01)
*A61L 27/32* (2006.01)
*A61F 2/30* (2006.01)

(52) U.S. Cl.
CPC ............ *A61F 2/447* (2013.01); *A61F 2/4455* (2013.01); *A61L 27/32* (2013.01);
(Continued)

(58) Field of Classification Search
CPC ...... A61F 2/44–2/447; A61F 2002/443; A61F 2002/4475
See application file for complete search history.

(56) References Cited

U.S. PATENT DOCUMENTS 1,802,560 A 4/1931 Kerwin
2,077,804 A 4/1937 Morrison
(Continued)

FOREIGN PATENT DOCUMENTS

AU 2005314079 A1 6/2006
CN 1177918 A 4/1998
(Continued)

OTHER PUBLICATIONS

Apr. 2, 2012 Office Action (to proceed and to respond to Search Report) for Application No. 05777628.8.
(Continued)

*Primary Examiner* — Nicholas J Plionis
*Assistant Examiner* — Steven J Cotroneo
(74) *Attorney, Agent, or Firm* — BakerHostetler

(57) ABSTRACT

An adjustable spinal fusion intervertebral implant including upper and lower body portions each having proximal and distal surfaces at proximal and distal ends thereof. The implant can include a proximal wedge member disposed at the proximal ends of the respective ones of the upper and lower body portions, and a distal wedge member disposed at the distal ends of the respective ones of the upper and lower body portions. First and second linkages can connect the upper and lower body portions. Rotation of an actuator shaft can cause the distal and proximal wedge members to be drawn together such that longitudinal movement of the distal wedge member against the distal surfaces and the longitudinal movement of the proximal wedge member against the proximal surfaces causes separation of the upper and lower body portions.

30 Claims, 13 Drawing Sheets

(52) U.S. Cl.
CPC ............... *A61F 2002/30064* (2013.01); *A61F 2002/30133* (2013.01); *A61F 2002/30281* (2013.01); *A61F 2002/30387* (2013.01); *A61F 2002/30393* (2013.01); *A61F 2002/30398* (2013.01); *A61F 2002/30411* (2013.01); *A61F 2002/30507* (2013.01); *A61F 2002/30556* (2013.01); *A61F 2002/30579* (2013.01); *A61F 2002/30774* (2013.01); *A61F 2002/30777* (2013.01); *A61F 2002/30779* (2013.01); *A61F 2002/30784* (2013.01); *A61F 2002/30828* (2013.01); *A61F 2002/30904* (2013.01); *A61F 2240/001* (2013.01); *Y10T 29/49826* (2015.01); *Y10T 29/49888* (2015.01)

(56) References Cited

U.S. PATENT DOCUMENTS

| | | | |
|---|---|---|---|
| 2,121,193 | A | 6/1938 | Hanicke |
| 2,173,655 | A | 9/1939 | Neracher et al. |
| 2,243,717 | A | 5/1941 | Moreira |
| 2,381,050 | A | 8/1945 | Hardinge |
| 2,388,056 | A | 10/1945 | Hendricks |
| 2,485,531 | A | 10/1949 | William et al. |
| 2,489,870 | A | 11/1949 | Dzus |
| 2,570,465 | A | 10/1951 | Lundholm |
| 2,677,369 | A | 5/1954 | Knowles |
| 3,115,804 | A | 12/1963 | Johnson |
| 3,312,139 | A | 4/1967 | Di Cristina |
| 3,486,505 | A | 12/1969 | Morrison |
| 3,489,143 | A | 1/1970 | Halloran |
| 3,698,391 | A | 10/1972 | Mahony |
| 3,760,802 | A | 9/1973 | Fischer et al. |
| 3,805,775 | A | 4/1974 | Fischer et al. |
| 3,811,449 | A | 5/1974 | Gravlee et al. |
| 3,842,825 | A | 10/1974 | Wagner |
| 3,848,601 | A | 11/1974 | Ma et al. |
| 3,986,504 | A | 10/1976 | Avila |
| 4,013,071 | A | 3/1977 | Rosenberg |
| 4,052,988 | A | 10/1977 | Doddi et al. |
| 4,091,806 | A | 5/1978 | Aginsky |
| 4,175,555 | A | 11/1979 | Herbert |
| 4,236,512 | A | 12/1980 | Aginsky |
| 4,262,665 | A | 4/1981 | Roalstad et al. |
| 4,275,717 | A | 6/1981 | Bolesky |
| 4,312,353 | A | 1/1982 | Shahbabian |
| 4,341,206 | A | 7/1982 | Perrett et al. |
| 4,350,151 | A | 9/1982 | Scott |
| 4,369,790 | A | 1/1983 | McCarthy |
| 4,401,112 | A | 8/1983 | Rezaian |
| 4,401,433 | A | 8/1983 | Luther |
| 4,409,974 | A | 10/1983 | Freedland |
| 4,449,532 | A | 5/1984 | Storz |
| 4,451,256 | A | 5/1984 | Weikl et al. |
| 4,456,005 | A | 6/1984 | Lichty |
| 4,463,753 | A | 8/1984 | Gustilo |
| 4,488,543 | A | 12/1984 | Tornier |
| 4,494,535 | A | 1/1985 | Haig |
| 4,532,660 | A | 8/1985 | Field |
| 4,537,185 | A | 8/1985 | Stednitz |
| 4,545,374 | A | 10/1985 | Jacobson |
| 4,573,448 | A | 3/1986 | Kambin |
| 4,601,710 | A | 7/1986 | Moll |
| 4,625,725 | A | 12/1986 | Davison et al. |
| 4,629,450 | A | 12/1986 | Suzuki et al. |
| 4,632,101 | A | 12/1986 | Freedland |
| 4,640,271 | A | 2/1987 | Lower |
| 4,641,640 | A | 2/1987 | Griggs |
| 4,646,741 | A | 3/1987 | Smith |
| 4,653,489 | A | 3/1987 | Tronzo |
| 4,667,663 | A | 5/1987 | Miyata |
| 4,686,984 | A | 8/1987 | Bonnet |
| 4,688,561 | A | 8/1987 | Reese |
| 4,721,103 | A | 1/1988 | Freedland |
| 4,723,544 | A | 2/1988 | Moore et al. |
| 4,743,257 | A | 5/1988 | Toermaelae et al. |
| 4,760,843 | A | 8/1988 | Fischer et al. |
| 4,790,304 | A | 12/1988 | Rosenberg |
| 4,790,817 | A | 12/1988 | Luther |
| 4,796,612 | A | 1/1989 | Reese |
| 4,802,479 | A | 2/1989 | Haber et al. |
| 4,815,909 | A | 3/1989 | Simons |
| 4,827,917 | A | 5/1989 | Brumfield |
| 4,858,601 | A | 8/1989 | Glisson |
| 4,862,891 | A | 9/1989 | Smith |
| 4,863,476 | A | 9/1989 | Shepperd |
| 4,873,976 | A | 10/1989 | Schreiber |
| 4,889,119 | A | 12/1989 | Jamiolkowski et al. |
| 4,898,186 | A | 2/1990 | Ikada et al. |
| 4,903,692 | A | 2/1990 | Reese |
| 4,917,554 | A | 4/1990 | Bronn |
| 4,940,467 | A | 7/1990 | Tronzo |
| 4,959,064 | A | 9/1990 | Engelhardt |
| 4,963,144 | A | 10/1990 | Huene |
| 4,966,587 | A | 10/1990 | Baumgart |
| 4,968,317 | A | 11/1990 | Toermaelae et al. |
| 4,978,334 | A | 12/1990 | Toye et al. |
| 4,978,349 | A | 12/1990 | Frigg |
| 4,981,482 | A | 1/1991 | Ichikawa |
| 4,988,351 | A | 1/1991 | Paulos et al. |
| 4,994,027 | A | 2/1991 | Farrell |
| 5,002,557 | A | 3/1991 | Hasson |
| 5,011,484 | A | 4/1991 | Breard |
| 5,013,315 | A | 5/1991 | Barrows |
| 5,013,316 | A | 5/1991 | Goble et al. |
| 5,059,193 | A | 10/1991 | Kuslich |
| 5,062,849 | A | 11/1991 | Schelhas |
| 5,080,662 | A | 1/1992 | Paul |
| 5,084,043 | A | 1/1992 | Hertzmann et al. |
| 5,092,891 | A | 3/1992 | Kummer et al. |
| 5,098,241 | A | 3/1992 | Aldridge et al. |
| 5,098,433 | A | 3/1992 | Freedland |
| 5,098,435 | A | 3/1992 | Stednitz et al. |
| 5,114,407 | A | 5/1992 | Burbank |
| 5,116,336 | A | 5/1992 | Frigg |
| 5,120,171 | A | 6/1992 | Lasner |
| 5,122,133 | A | 6/1992 | Evans |
| 5,122,141 | A | 6/1992 | Simpson et al. |
| 5,139,486 | A | 8/1992 | Moss |
| 5,158,543 | A | 10/1992 | Lazarus |
| 5,167,663 | A | 12/1992 | Brumfield |
| 5,167,664 | A | 12/1992 | Hodorek |
| 5,169,400 | A | 12/1992 | Muehling et al. |
| 5,171,278 | A | 12/1992 | Pisharodi |
| 5,171,279 | A | 12/1992 | Mathews |
| 5,171,280 | A | 12/1992 | Baumgartner |
| 5,176,651 | A | 1/1993 | Allgood et al. |
| 5,176,697 | A | 1/1993 | Hasson et al. |
| 5,178,501 | A | 1/1993 | Carstairs |
| 5,183,464 | A | 2/1993 | Dubrul et al. |
| 5,188,118 | A | 2/1993 | Terwilliger |
| 5,195,506 | A | 3/1993 | Hulfish |
| 5,201,742 | A | 4/1993 | Hasson |
| 5,217,462 | A | 6/1993 | Asnis et al. |
| 5,217,486 | A | 6/1993 | Rice et al. |
| 5,224,952 | A | 7/1993 | Deniega et al. |
| 5,234,431 | A | 8/1993 | Keller |
| 5,241,972 | A | 9/1993 | Bonati |
| 5,242,410 | A | 9/1993 | Melker |
| 5,242,447 | A | 9/1993 | Borzone |
| 5,246,441 | A | 9/1993 | Ross et al. |
| 5,250,049 | A | 10/1993 | Michael |
| 5,269,797 | A | 12/1993 | Bonati et al. |
| 5,280,782 | A | 1/1994 | Wilk |
| 5,286,001 | A | 2/1994 | Rafeld |
| 5,290,243 | A | 3/1994 | Chodorow et al. |
| 5,300,074 | A | 4/1994 | Frigg |
| 5,304,142 | A | 4/1994 | Liebl et al. |
| 5,308,327 | A | 5/1994 | Heaven et al. |
| 5,308,352 | A | 5/1994 | Koutrouvelis |
| 5,312,410 | A | 5/1994 | Miller et al. |
| 5,312,417 | A | 5/1994 | Wilk |
| 5,324,261 | A | 6/1994 | Amundson et al. |
| 5,334,184 | A | 8/1994 | Bimman |

(56) References Cited

U.S. PATENT DOCUMENTS

| | | | |
|---|---|---|---|
| 5,334,204 | A | 8/1994 | Clewett et al. |
| 5,342,365 | A | 8/1994 | Waldman |
| 5,342,382 | A | 8/1994 | Brinkerhoff et al. |
| 5,344,252 | A | 9/1994 | Kakimoto |
| 5,364,398 | A | 11/1994 | Chapman et al. |
| 5,370,646 | A | 12/1994 | Reese et al. |
| 5,370,647 | A | 12/1994 | Graber et al. |
| 5,370,661 | A | 12/1994 | Branch |
| 5,382,248 | A | 1/1995 | Jacobson et al. |
| 5,387,213 | A | 2/1995 | Breard et al. |
| 5,387,215 | A | 2/1995 | Fisher |
| 5,390,683 | A | 2/1995 | Pisharodi |
| 5,395,317 | A | 3/1995 | Kambin |
| 5,395,371 | A | 3/1995 | Miller et al. |
| 5,407,430 | A | 4/1995 | Peters |
| 5,415,661 | A | 5/1995 | Holmes |
| 5,424,773 | A | 6/1995 | Saito |
| 5,449,359 | A | 9/1995 | Groiso |
| 5,449,361 | A | 9/1995 | Preissman |
| 5,452,748 | A | 9/1995 | Simmons et al. |
| 5,454,790 | A | 10/1995 | Dubrul |
| 5,464,427 | A | 11/1995 | Curtis et al. |
| 5,470,333 | A | 11/1995 | Ray |
| 5,472,426 | A | 12/1995 | Bonati et al. |
| 5,474,539 | A | 12/1995 | Costa et al. |
| 5,486,190 | A | 1/1996 | Green |
| 5,496,318 | A | 3/1996 | Howland et al. |
| 5,498,265 | A | 3/1996 | Asnis et al. |
| 5,501,695 | A | 3/1996 | Anspach et al. |
| 5,505,710 | A | 4/1996 | Dorsey, III |
| 5,512,037 | A | 4/1996 | Russell et al. |
| 5,514,180 | A | 5/1996 | Heggeness et al. |
| 5,520,690 | A | 5/1996 | Errico et al. |
| 5,520,896 | A | 5/1996 | De et al. |
| 5,527,312 | A | 6/1996 | Ray |
| 5,536,127 | A | 7/1996 | Pennig |
| 5,540,688 | A | 7/1996 | Navas |
| 5,540,693 | A | 7/1996 | Fisher |
| 5,545,164 | A | 8/1996 | Howland |
| 5,549,610 | A | 8/1996 | Russell et al. |
| 5,554,191 | A | 9/1996 | Lahille et al. |
| 5,558,674 | A | 9/1996 | Heggeness et al. |
| D374,287 | S | 10/1996 | Goble et al. |
| 5,564,926 | A | 10/1996 | Braanemark |
| 5,569,248 | A | 10/1996 | Mathews |
| 5,569,251 | A | 10/1996 | Baker et al. |
| 5,569,290 | A | 10/1996 | McAfee |
| 5,569,548 | A | 10/1996 | Koike et al. |
| 5,591,168 | A | 1/1997 | Judet et al. |
| 5,609,634 | A | 3/1997 | Voydeville |
| 5,613,950 | A | 3/1997 | Yoon |
| 5,618,142 | A | 4/1997 | Sonden et al. |
| 5,618,314 | A | 4/1997 | Harwin et al. |
| 5,624,447 | A | 4/1997 | Myers |
| 5,626,613 | A | 5/1997 | Schmieding |
| 5,628,751 | A | 5/1997 | Sander et al. |
| 5,628,752 | A | 5/1997 | Asnis et al. |
| 5,639,276 | A | 6/1997 | Weinstock et al. |
| 5,643,320 | A | 7/1997 | Lower et al. |
| 5,645,589 | A | 7/1997 | Li |
| 5,645,599 | A | 7/1997 | Samani |
| 5,647,857 | A | 7/1997 | Anderson et al. |
| 5,649,931 | A | 7/1997 | Bryant et al. |
| 5,653,763 | A | 8/1997 | Errico et al. |
| 5,658,335 | A | 8/1997 | Allen |
| 5,665,095 | A | 9/1997 | Jacobson et al. |
| 5,665,122 | A | 9/1997 | Kambin |
| 5,667,508 | A | 9/1997 | Errico et al. |
| 5,669,915 | A | 9/1997 | Caspar et al. |
| 5,693,100 | A | 12/1997 | Pisharodi |
| 5,702,391 | A | 12/1997 | Lin |
| 5,707,359 | A | 1/1998 | Bufalini |
| 5,713,870 | A | 2/1998 | Yoon |
| 5,713,903 | A | 2/1998 | Sander et al. |
| 5,716,415 | A | 2/1998 | Steffee |
| 5,716,416 | A | 2/1998 | Lin |
| 5,720,753 | A | 2/1998 | Sander et al. |
| 5,725,541 | A | 3/1998 | Anspach et al. |
| 5,725,588 | A | 3/1998 | Errico et al. |
| 5,728,097 | A | 3/1998 | Mathews |
| 5,728,116 | A | 3/1998 | Rosenman |
| 5,735,853 | A | 4/1998 | Olerud |
| 5,741,282 | A | 4/1998 | Anspach et al. |
| 5,743,881 | A | 4/1998 | Demco |
| 5,743,912 | A | 4/1998 | Lahille et al. |
| 5,743,914 | A | 4/1998 | Skiba |
| 5,749,889 | A | 5/1998 | Bacich et al. |
| 5,752,969 | A | 5/1998 | Cunci et al. |
| 5,762,500 | A | 6/1998 | Lazarof |
| 5,762,629 | A | 6/1998 | Kambin |
| 5,772,662 | A | 6/1998 | Chapman et al. |
| 5,772,678 | A | 6/1998 | Thomason et al. |
| 5,776,156 | A | 7/1998 | Shikhman |
| 5,782,800 | A | 7/1998 | Yoon |
| 5,782,865 | A | 7/1998 | Grotz |
| 5,792,044 | A | 8/1998 | Foley et al. |
| 5,810,721 | A | 9/1998 | Mueller et al. |
| 5,810,821 | A | 9/1998 | Vandewalle |
| 5,810,866 | A | 9/1998 | Yoon |
| 5,814,084 | A | 9/1998 | Grivas et al. |
| 5,836,948 | A | 11/1998 | Zucherman et al. |
| 5,846,259 | A | 12/1998 | Berthiaume |
| 5,849,004 | A | 12/1998 | Bramlet |
| 5,851,216 | A | 12/1998 | Allen |
| 5,860,977 | A | 1/1999 | Zucherman et al. |
| 5,865,848 | A | 2/1999 | Baker |
| 5,871,485 | A | 2/1999 | Rao et al. |
| 5,873,854 | A | 2/1999 | Wolvek |
| 5,876,404 | A | 3/1999 | Zucherman et al. |
| 5,888,228 | A | 3/1999 | Knothe et al. |
| 5,893,850 | A | 4/1999 | Cachia |
| 5,893,889 | A | 4/1999 | Harrington |
| 5,895,428 | A | 4/1999 | Berry |
| 5,902,231 | A | 5/1999 | Foley et al. |
| 5,904,696 | A | 5/1999 | Rosenman |
| 5,908,422 | A | 6/1999 | Bresina |
| 5,928,235 | A | 7/1999 | Friedl |
| 5,928,244 | A | 7/1999 | Tovey et al. |
| 5,931,870 | A | 8/1999 | Cuckler et al. |
| 5,935,129 | A | 8/1999 | McDevitt et al. |
| 5,947,999 | A | 9/1999 | Groiso |
| 5,948,000 | A | 9/1999 | Larsen et al. |
| 5,954,722 | A | 9/1999 | Bono |
| 5,954,747 | A | 9/1999 | Clark |
| 5,957,902 | A | 9/1999 | Teves |
| 5,957,924 | A | 9/1999 | Toermaelae et al. |
| 5,964,730 | A | 10/1999 | Williams et al. |
| 5,964,761 | A | 10/1999 | Kambin |
| 5,967,783 | A | 10/1999 | Ura |
| 5,967,970 | A | 10/1999 | Cowan et al. |
| 5,968,044 | A | 10/1999 | Nicholson et al. |
| 5,968,098 | A | 10/1999 | Winslow |
| 5,976,139 | A | 11/1999 | Bramlet |
| 5,976,146 | A | 11/1999 | Ogawa et al. |
| 5,976,186 | A | 11/1999 | Bao et al. |
| 5,980,522 | A | 11/1999 | Koros et al. |
| 5,984,927 | A | 11/1999 | Wenstrom et al. |
| 5,984,966 | A | 11/1999 | Kiema et al. |
| 5,989,255 | A | 11/1999 | Pepper et al. |
| 5,993,459 | A | 11/1999 | Larsen et al. |
| 5,997,510 | A | 12/1999 | Schwemberger |
| 5,997,538 | A | 12/1999 | Asnis et al. |
| 5,997,541 | A | 12/1999 | Schenk |
| 6,001,100 | A | 12/1999 | Sherman et al. |
| 6,001,101 | A | 12/1999 | Augagneur et al. |
| 6,004,327 | A | 12/1999 | Asnis et al. |
| 6,005,161 | A | 12/1999 | Brekke |
| 6,007,519 | A | 12/1999 | Rosselli |
| 6,007,566 | A | 12/1999 | Wenstrom, Jr. |
| 6,007,580 | A | 12/1999 | Lehto et al. |
| 6,010,513 | A | 1/2000 | Toermaelae et al. |
| 6,015,410 | A | 1/2000 | Toermaelae et al. |
| 6,019,762 | A | 2/2000 | Cole |
| 6,022,352 | A | 2/2000 | Vandewalle |

(56) References Cited

U.S. PATENT DOCUMENTS

| | | |
|---|---|---|
| 6,030,162 A | 2/2000 | Huebner |
| 6,030,364 A | 2/2000 | Durgin et al. |
| 6,033,406 A | 3/2000 | Mathews |
| 6,036,701 A | 3/2000 | Rosenman |
| 6,048,309 A | 4/2000 | Flom et al. |
| 6,048,342 A | 4/2000 | Zucherman et al. |
| 6,053,935 A | 4/2000 | Brenneman et al. |
| 6,066,142 A | 5/2000 | Serbousek et al. |
| 6,068,630 A | 5/2000 | Zucherman et al. |
| 6,068,648 A | 5/2000 | Cole et al. |
| 6,074,390 A | 6/2000 | Zucherman et al. |
| 6,080,193 A | 6/2000 | Hochschuler et al. |
| 6,083,244 A | 7/2000 | Lubbers et al. |
| 6,090,112 A | 7/2000 | Zucherman et al. |
| 6,102,914 A | 8/2000 | Bulstra et al. |
| 6,102,950 A | 8/2000 | Vaccaro |
| 6,117,174 A | 9/2000 | Nolan |
| 6,123,711 A | 9/2000 | Winters |
| 6,126,661 A | 10/2000 | Faccioli et al. |
| 6,126,663 A | 10/2000 | Hair |
| 6,129,762 A | 10/2000 | Li |
| 6,129,763 A | 10/2000 | Chauvin et al. |
| 6,146,384 A | 11/2000 | Lee et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,179 A | 12/2000 | Simonson |
| 6,161,350 A | 12/2000 | Espinosa |
| 6,162,234 A | 12/2000 | Freedland et al. |
| 6,162,236 A | 12/2000 | Osada |
| 6,168,595 B1 | 1/2001 | Durham et al. |
| 6,168,597 B1 | 1/2001 | Biedermann et al. |
| 6,175,758 B1 | 1/2001 | Kambin |
| 6,176,882 B1 * | 1/2001 | Biedermann ............ A61F 2/447 623/17.11 |
| 6,183,471 B1 | 2/2001 | Zucherman et al. |
| 6,183,472 B1 | 2/2001 | Lutz |
| 6,183,474 B1 | 2/2001 | Bramlet et al. |
| 6,190,387 B1 | 2/2001 | Zucherman et al. |
| 6,197,041 B1 | 3/2001 | Shichman et al. |
| 6,200,322 B1 | 3/2001 | Branch et al. |
| 6,206,826 B1 | 3/2001 | Mathews et al. |
| 6,206,922 B1 | 3/2001 | Zdeblick et al. |
| 6,213,957 B1 | 4/2001 | Milliman et al. |
| 6,217,509 B1 | 4/2001 | Foley et al. |
| 6,221,082 B1 | 4/2001 | Marino et al. |
| 6,228,058 B1 | 5/2001 | Dennis et al. |
| 6,231,606 B1 | 5/2001 | Graf et al. |
| 6,235,030 B1 | 5/2001 | Zucherman et al. |
| 6,238,397 B1 | 5/2001 | Zucherman et al. |
| 6,245,107 B1 | 6/2001 | Ferree |
| 6,248,108 B1 | 6/2001 | Toermaelae et al. |
| 6,251,111 B1 | 6/2001 | Barker et al. |
| 6,264,676 B1 | 7/2001 | Gellman et al. |
| 6,267,765 B1 | 7/2001 | Taylor et al. |
| 6,267,767 B1 | 7/2001 | Strobel et al. |
| 6,280,444 B1 | 8/2001 | Zucherman et al. |
| 6,287,313 B1 | 9/2001 | Sasso |
| 6,293,909 B1 | 9/2001 | Chu et al. |
| 6,293,952 B1 | 9/2001 | Brosens et al. |
| 6,306,136 B1 | 10/2001 | Baccelli |
| 6,319,254 B1 | 11/2001 | Giet et al. |
| 6,319,272 B1 | 11/2001 | Brenneman et al. |
| 6,332,882 B1 | 12/2001 | Zucherman et al. |
| 6,332,883 B1 | 12/2001 | Zucherman et al. |
| 6,346,092 B1 | 2/2002 | Leschinsky |
| 6,348,053 B1 | 2/2002 | Cachia |
| 6,355,043 B1 | 3/2002 | Adam |
| 6,361,537 B1 | 3/2002 | Anderson |
| 6,361,538 B1 | 3/2002 | Fenaroli et al. |
| 6,361,557 B1 | 3/2002 | Gittings et al. |
| 6,364,897 B1 | 4/2002 | Bonutti |
| 6,368,351 B1 | 4/2002 | Glenn et al. |
| 6,371,971 B1 | 4/2002 | Tsugita et al. |
| 6,371,989 B1 | 4/2002 | Chauvin et al. |
| 6,375,682 B1 | 4/2002 | Fleischmann et al. |
| 6,379,355 B1 | 4/2002 | Zucherman et al. |
| 6,379,363 B1 | 4/2002 | Herrington et al. |
| 6,387,130 B1 | 5/2002 | Stone et al. |
| 6,409,767 B1 | 6/2002 | Perice et al. |
| 6,419,676 B1 | 7/2002 | Zucherman et al. |
| 6,419,677 B2 | 7/2002 | Zucherman et al. |
| 6,419,704 B1 | 7/2002 | Ferree |
| 6,423,061 B1 | 7/2002 | Bryant |
| 6,423,067 B1 | 7/2002 | Eisermann |
| 6,425,919 B1 | 7/2002 | Lambrecht |
| 6,428,541 B1 | 8/2002 | Boyd et al. |
| 6,428,556 B1 | 8/2002 | Chin |
| 6,436,143 B1 | 8/2002 | Ross et al. |
| 6,440,154 B2 | 8/2002 | Gellman et al. |
| 6,440,169 B1 | 8/2002 | Elberg et al. |
| 6,443,989 B1 | 9/2002 | Jackson |
| 6,447,527 B1 | 9/2002 | Thompson et al. |
| 6,447,540 B1 | 9/2002 | Fontaine et al. |
| 6,450,989 B2 | 9/2002 | Dubrul et al. |
| 6,451,019 B1 | 9/2002 | Zucherman et al. |
| 6,451,020 B1 | 9/2002 | Zucherman et al. |
| 6,454,807 B1 | 9/2002 | Jackson |
| 6,458,134 B1 | 10/2002 | Songer et al. |
| 6,468,277 B1 | 10/2002 | Justin et al. |
| 6,468,309 B1 | 10/2002 | Lieberman |
| 6,468,310 B1 | 10/2002 | Ralph et al. |
| 6,471,724 B2 | 10/2002 | Zdeblick et al. |
| 6,475,226 B1 | 11/2002 | Belef et al. |
| 6,478,029 B1 | 11/2002 | Boyd et al. |
| 6,478,796 B2 | 11/2002 | Zucherman et al. |
| 6,485,491 B1 | 11/2002 | Farris et al. |
| 6,485,518 B1 | 11/2002 | Cornwall et al. |
| 6,488,693 B2 | 12/2002 | Gannoe et al. |
| 6,491,714 B1 | 12/2002 | Bennett |
| 6,494,860 B2 | 12/2002 | Rocamora et al. |
| 6,494,893 B2 | 12/2002 | Dubrul et al. |
| 6,500,178 B2 | 12/2002 | Zucherman et al. |
| 6,506,192 B1 | 1/2003 | Gertzman et al. |
| 6,511,481 B2 | 1/2003 | Von et al. |
| 6,514,256 B2 | 2/2003 | Zucherman et al. |
| 6,517,543 B1 | 2/2003 | Berrevoets et al. |
| 6,520,907 B1 | 2/2003 | Foley et al. |
| 6,527,774 B2 | 3/2003 | Lieberman |
| 6,540,747 B1 | 4/2003 | Marino |
| 6,544,265 B2 | 4/2003 | Lieberman |
| 6,547,793 B1 | 4/2003 | McGuire |
| 6,547,795 B2 | 4/2003 | Schneiderman |
| 6,551,319 B2 | 4/2003 | Lieberman |
| 6,551,322 B1 | 4/2003 | Lieberman |
| 6,554,831 B1 | 4/2003 | Rivard et al. |
| 6,554,852 B1 | 4/2003 | Oberlander |
| 6,558,389 B2 | 5/2003 | Clark et al. |
| 6,562,046 B2 | 5/2003 | Sasso |
| 6,562,049 B1 | 5/2003 | Norlander et al. |
| 6,562,074 B2 | 5/2003 | Gerbec et al. |
| 6,575,979 B1 | 6/2003 | Cragg |
| 6,576,016 B1 | 6/2003 | Hochshuler et al. |
| 6,579,293 B1 | 6/2003 | Chandran |
| 6,582,390 B1 | 6/2003 | Sanderson |
| 6,582,431 B1 | 6/2003 | Ray |
| 6,582,433 B2 | 6/2003 | Yun |
| 6,582,437 B2 | 6/2003 | Dorchak et al. |
| 6,582,441 B1 | 6/2003 | He et al. |
| 6,582,453 B1 | 6/2003 | Tran et al. |
| 6,585,730 B1 | 7/2003 | Foerster |
| 6,585,740 B2 | 7/2003 | Schlapfer et al. |
| 6,589,240 B2 | 7/2003 | Hinchliffe |
| 6,589,249 B2 | 7/2003 | Sater et al. |
| 6,592,553 B2 | 7/2003 | Zhang et al. |
| 6,595,998 B2 | 7/2003 | Johnson et al. |
| 6,596,008 B1 | 7/2003 | Kambin |
| 6,599,297 B1 | 7/2003 | Carlsson et al. |
| 6,607,530 B1 | 8/2003 | Carl et al. |
| 6,610,091 B1 | 8/2003 | Reiley |
| 6,613,050 B1 | 9/2003 | Wagner et al. |
| 6,616,678 B2 | 9/2003 | Nishtala et al. |
| 6,620,196 B1 | 9/2003 | Trieu |
| 6,626,944 B1 | 9/2003 | Taylor |

(56) References Cited

U.S. PATENT DOCUMENTS

| | | |
|---|---|---|
| 6,632,224 B2 | 10/2003 | Cachia et al. |
| 6,635,059 B2 | 10/2003 | Randall et al. |
| 6,635,362 B2 | 10/2003 | Zheng |
| 6,648,890 B2 | 11/2003 | Culbert et al. |
| 6,648,893 B2 | 11/2003 | Dudasik |
| 6,652,527 B2 | 11/2003 | Zucherman et al. |
| 6,655,962 B1 | 12/2003 | Kennard |
| 6,666,891 B2 | 12/2003 | Boehm et al. |
| 6,669,698 B1 | 12/2003 | Tromanhauser et al. |
| 6,669,729 B2 | 12/2003 | Chin |
| 6,673,074 B2 | 1/2004 | Shluzas |
| 6,676,664 B1 | 1/2004 | Al-Assir |
| 6,679,833 B2 | 1/2004 | Smith et al. |
| 6,682,535 B2 | 1/2004 | Hoogland |
| 6,685,706 B2 | 2/2004 | Padget et al. |
| 6,685,742 B1 | 2/2004 | Jackson |
| 6,689,152 B2 | 2/2004 | Balceta et al. |
| 6,692,499 B2 | 2/2004 | Toermaelae et al. |
| 6,695,842 B2 | 2/2004 | Zucherman et al. |
| 6,695,851 B2 | 2/2004 | Zdeblick et al. |
| 6,699,246 B2 | 3/2004 | Zucherman et al. |
| 6,699,247 B2 | 3/2004 | Zucherman et al. |
| 6,712,819 B2 | 3/2004 | Zucherman et al. |
| 6,716,247 B2 | 4/2004 | Michelson |
| 6,719,760 B2 | 4/2004 | Dorchak et al. |
| 6,723,096 B1 | 4/2004 | Dorchak et al. |
| 6,723,126 B1 | 4/2004 | Berry |
| 6,730,126 B2 | 5/2004 | Boehm et al. |
| 6,733,534 B2 | 5/2004 | Sherman |
| 6,733,535 B2 | 5/2004 | Michelson |
| 6,733,635 B1 | 5/2004 | Ozawa et al. |
| 6,740,090 B1 | 5/2004 | Cragg et al. |
| 6,740,093 B2 | 5/2004 | Hochschuler et al. |
| 6,743,166 B2 | 6/2004 | Berci et al. |
| 6,746,451 B2 | 6/2004 | Middleton et al. |
| 6,752,831 B2 | 6/2004 | Sybert et al. |
| 6,761,720 B1 | 7/2004 | Senegas |
| 6,770,075 B2 | 8/2004 | Howland |
| 6,773,460 B2 | 8/2004 | Jackson |
| 6,790,210 B1 | 9/2004 | Cragg et al. |
| 6,793,656 B1 | 9/2004 | Mathews |
| 6,796,983 B1 | 9/2004 | Zucherman et al. |
| 6,805,695 B2 | 10/2004 | Keith et al. |
| 6,808,526 B1 | 10/2004 | Magerl et al. |
| 6,808,537 B2 | 10/2004 | Michelson |
| 6,821,298 B1 | 11/2004 | Jackson |
| 6,830,589 B2 | 12/2004 | Erickson |
| 6,835,205 B2 | 12/2004 | Atkinson et al. |
| 6,835,206 B2 | 12/2004 | Jackson |
| 6,875,215 B2 | 4/2005 | Taras et al. |
| 6,887,243 B2 | 5/2005 | Culbert |
| 6,890,333 B2 | 5/2005 | Von et al. |
| 6,893,466 B2 | 5/2005 | Trieu |
| 6,902,566 B2 | 6/2005 | Zucherman et al. |
| 6,908,465 B2 | 6/2005 | Von et al. |
| 6,916,323 B2 | 7/2005 | Kitchens |
| 6,921,403 B2 | 7/2005 | Cragg et al. |
| 6,923,811 B1 | 8/2005 | Carl et al. |
| 6,929,606 B2 | 8/2005 | Ritland |
| 6,936,072 B2 | 8/2005 | Lambrecht et al. |
| 6,942,668 B2 | 9/2005 | Padget et al. |
| 6,945,975 B2 | 9/2005 | Dalton |
| 6,946,000 B2 | 9/2005 | Senegas et al. |
| 6,949,100 B1 | 9/2005 | Venturini |
| 6,951,561 B2 | 10/2005 | Warren et al. |
| 6,972,035 B2 | 12/2005 | Michelson |
| 6,997,929 B2 | 2/2006 | Manzi et al. |
| 7,004,945 B2 | 2/2006 | Boyd et al. |
| 7,018,415 B1 | 3/2006 | McKay |
| 7,025,746 B2 | 4/2006 | Tal |
| 7,029,473 B2 | 4/2006 | Zucherman et al. |
| 7,041,107 B2 | 5/2006 | Pohjonen et al. |
| 7,048,736 B2 | 5/2006 | Robinson et al. |
| 7,060,068 B2 | 6/2006 | Tromanhauser et al. |
| 7,063,701 B2 | 6/2006 | Michelson |
| 7,063,702 B2 | 6/2006 | Michelson |
| 7,066,960 B1 | 6/2006 | Dickman |
| 7,066,961 B2 | 6/2006 | Michelson |
| 7,070,601 B2 | 7/2006 | Culbert et al. |
| 7,074,203 B1 | 7/2006 | Johanson et al. |
| 7,087,083 B2 | 8/2006 | Pasquet et al. |
| 7,094,239 B1 | 8/2006 | Michelson |
| 7,094,257 B2 | 8/2006 | Mujwid et al. |
| 7,094,258 B2 | 8/2006 | Lambrecht et al. |
| 7,101,375 B2 | 9/2006 | Zucherman et al. |
| 7,114,501 B2 | 10/2006 | Johnson et al. |
| 7,118,572 B2 | 10/2006 | Bramlet et al. |
| 7,118,579 B2 | 10/2006 | Michelson |
| 7,118,598 B2 | 10/2006 | Michelson |
| 7,128,760 B2 | 10/2006 | Michelson |
| 7,153,305 B2 | 12/2006 | Johnson et al. |
| D536,096 S | 1/2007 | Hoogland et al. |
| 7,163,558 B2 | 1/2007 | Senegas et al. |
| 7,172,612 B2 | 2/2007 | Ishikawa |
| 7,175,625 B2 | 2/2007 | Culbert |
| 7,179,294 B2 | 2/2007 | Eisermann et al. |
| 7,201,751 B2 | 4/2007 | Zucherman et al. |
| 7,226,481 B2 | 6/2007 | Kuslich |
| 7,238,204 B2 | 7/2007 | Le et al. |
| 7,267,683 B2 | 9/2007 | Sharkey et al. |
| 7,282,061 B2 | 10/2007 | Sharkey et al. |
| 7,306,628 B2 | 12/2007 | Zucherman et al. |
| 7,309,357 B2 | 12/2007 | Kim |
| 7,326,211 B2 | 2/2008 | Padget et al. |
| 7,335,203 B2 | 2/2008 | Winslow et al. |
| 7,361,140 B2 | 4/2008 | Ries et al. |
| 7,371,238 B2 | 5/2008 | Soboleski et al. |
| 7,377,942 B2 | 5/2008 | Berry |
| 7,400,930 B2 | 7/2008 | Sharkey et al. |
| 7,410,501 B2 | 8/2008 | Michelson |
| 7,413,576 B2 | 8/2008 | Sybert et al. |
| 7,422,594 B2 | 9/2008 | Zander |
| 7,434,325 B2 | 10/2008 | Foley et al. |
| 7,445,636 B2 | 11/2008 | Michelson |
| 7,445,637 B2 | 11/2008 | Taylor |
| D584,812 S | 1/2009 | Ries |
| 7,473,256 B2 | 1/2009 | Assell et al. |
| 7,473,268 B2 | 1/2009 | Zucherman et al. |
| 7,476,251 B2 | 1/2009 | Zucherman et al. |
| 7,488,326 B2 | 2/2009 | Elliott |
| 7,520,888 B2 | 4/2009 | Trieu |
| 7,547,317 B2 | 6/2009 | Cragg |
| 7,556,629 B2 | 7/2009 | Von et al. |
| 7,556,651 B2 | 7/2009 | Humphreys et al. |
| 7,588,574 B2 | 9/2009 | Assell et al. |
| 7,625,378 B2 | 12/2009 | Foley |
| 7,641,657 B2 | 1/2010 | Cragg |
| 7,641,670 B2 | 1/2010 | Davison et al. |
| 7,647,123 B2 | 1/2010 | Sharkey et al. |
| 7,648,523 B2 | 1/2010 | Mirkovic et al. |
| 7,670,354 B2 | 3/2010 | Davison et al. |
| 7,674,273 B2 | 3/2010 | Davison et al. |
| 7,682,370 B2 | 3/2010 | Pagliuca et al. |
| 7,686,807 B2 | 3/2010 | Padget et al. |
| 7,691,120 B2 | 4/2010 | Shluzas et al. |
| 7,699,878 B2 | 4/2010 | Pavlov et al. |
| 7,717,944 B2 | 5/2010 | Foley et al. |
| 7,722,530 B2 | 5/2010 | Davison |
| 7,727,263 B2 | 6/2010 | Cragg |
| 7,740,633 B2 | 6/2010 | Assell et al. |
| 7,744,599 B2 | 6/2010 | Cragg |
| 7,762,995 B2 | 7/2010 | Eversull et al. |
| 7,763,025 B2 | 7/2010 | Ainsworth |
| 7,763,055 B2 | 7/2010 | Foley |
| 7,766,930 B2 | 8/2010 | Dipoto et al. |
| 7,771,479 B2 | 8/2010 | Humphreys et al. |
| 7,794,463 B2 | 9/2010 | Cragg |
| 7,799,032 B2 | 9/2010 | Assell et al. |
| 7,799,033 B2 | 9/2010 | Assell et al. |
| 7,799,036 B2 | 9/2010 | Davison et al. |
| D626,233 S | 10/2010 | Cipoletti et al. |
| 7,814,429 B2 | 10/2010 | Buffet et al. |
| 7,819,921 B2 | 10/2010 | Grotz |
| 7,824,410 B2 | 11/2010 | Simonson et al. |

(56) References Cited

U.S. PATENT DOCUMENTS

| | | |
|---|---|---|
| 7,824,429 B2 | 11/2010 | Culbert et al. |
| 7,837,734 B2 | 11/2010 | Zucherman et al. |
| 7,846,183 B2 | 12/2010 | Blain |
| 7,850,695 B2 | 12/2010 | Pagliuca et al. |
| 7,850,733 B2 | 12/2010 | Baynham et al. |
| 7,857,832 B2 | 12/2010 | Culbert et al. |
| 7,862,590 B2 | 1/2011 | Lim et al. |
| 7,862,595 B2 | 1/2011 | Foley et al. |
| 7,867,259 B2 | 1/2011 | Foley et al. |
| 7,875,077 B2 | 1/2011 | Humphreys et al. |
| 7,892,171 B2 | 2/2011 | Davison et al. |
| 7,892,249 B2 | 2/2011 | Davison et al. |
| 7,901,438 B2 | 3/2011 | Culbert et al. |
| 7,901,459 B2 | 3/2011 | Hodges et al. |
| 7,931,689 B2 | 4/2011 | Hochschuler et al. |
| 7,938,832 B2 | 5/2011 | Culbert et al. |
| 7,993,377 B2 | 8/2011 | Culbert et al. |
| 7,998,176 B2 | 8/2011 | Culbert |
| 8,062,375 B2 | 11/2011 | Glerum et al. |
| 8,105,382 B2 * | 1/2012 | Olmos .................. A61F 2/4611 623/17.15 |
| 8,109,977 B2 | 2/2012 | Culbert et al. |
| 8,133,232 B2 | 3/2012 | Levy et al. |
| 8,147,549 B2 | 4/2012 | Metcalf et al. |
| 8,231,675 B2 | 7/2012 | Rhoda |
| 8,257,440 B2 | 9/2012 | Gordon |
| 8,262,736 B2 | 9/2012 | Michelson |
| 8,273,129 B2 | 9/2012 | Baynham et al. |
| 8,317,866 B2 | 11/2012 | Palmatier et al. |
| 8,366,777 B2 | 2/2013 | Matthis et al. |
| 8,394,129 B2 | 3/2013 | Morgenstern et al. |
| 8,398,713 B2 | 3/2013 | Weiman |
| 8,518,087 B2 | 8/2013 | Lopez et al. |
| 8,551,092 B2 | 10/2013 | Morgan et al. |
| 8,551,094 B2 | 10/2013 | Von et al. |
| 8,709,088 B2 | 4/2014 | Kleiner et al. |
| 8,715,284 B2 | 5/2014 | Culbert |
| 8,926,704 B2 * | 1/2015 | Glerum .................. A61F 2/4455 606/279 |
| 9,387,313 B2 | 7/2016 | Culbert et al. |
| 9,445,825 B2 | 9/2016 | Belaney et al. |
| 9,522,070 B2 | 12/2016 | Flower et al. |
| 2001/0012950 A1 | 8/2001 | Nishtala et al. |
| 2001/0027320 A1 | 10/2001 | Sasso |
| 2001/0037126 A1 | 11/2001 | Stack et al. |
| 2001/0039452 A1 | 11/2001 | Zucherman et al. |
| 2002/0001476 A1 | 1/2002 | Nagamine et al. |
| 2002/0032462 A1 | 3/2002 | Houser et al. |
| 2002/0055740 A1 | 5/2002 | Lieberman |
| 2002/0087152 A1 | 7/2002 | Mikus et al. |
| 2002/0091387 A1 | 7/2002 | Hoogland |
| 2002/0120335 A1 | 8/2002 | Angelucci et al. |
| 2002/0143331 A1 | 10/2002 | Zucherman et al. |
| 2002/0161444 A1 | 10/2002 | Choi |
| 2002/0183848 A1 | 12/2002 | Ray et al. |
| 2003/0028250 A1 | 2/2003 | Reiley et al. |
| 2003/0063582 A1 | 4/2003 | Mizell et al. |
| 2003/0065330 A1 | 4/2003 | Zucherman et al. |
| 2003/0065396 A1 | 4/2003 | Michelson |
| 2003/0083688 A1 | 5/2003 | Simonson |
| 2003/0139648 A1 | 7/2003 | Foley et al. |
| 2003/0139813 A1 | 7/2003 | Messerli et al. |
| 2003/0187431 A1 | 10/2003 | Simonson |
| 2003/0208122 A1 | 11/2003 | Melkent et al. |
| 2003/0208220 A1 | 11/2003 | Worley et al. |
| 2003/0220643 A1 | 11/2003 | Ferree |
| 2003/0229350 A1 | 12/2003 | Kay |
| 2003/0233102 A1 | 12/2003 | Nakamura et al. |
| 2004/0006391 A1 | 1/2004 | Reiley |
| 2004/0008949 A1 | 1/2004 | Liu et al. |
| 2004/0019359 A1 | 1/2004 | Worley et al. |
| 2004/0024463 A1 | 2/2004 | Thomas et al. |
| 2004/0049190 A1 | 3/2004 | Biedermann et al. |
| 2004/0049223 A1 | 3/2004 | Nishtala et al. |
| 2004/0054412 A1 | 3/2004 | Gerbec et al. |
| 2004/0059339 A1 | 3/2004 | Roehm et al. |
| 2004/0059350 A1 | 3/2004 | Gordon et al. |
| 2004/0097924 A1 | 5/2004 | Lambrecht et al. |
| 2004/0097941 A1 | 5/2004 | Weiner et al. |
| 2004/0097973 A1 | 5/2004 | Loshakove et al. |
| 2004/0127906 A1 | 7/2004 | Culbert |
| 2004/0133280 A1 | 7/2004 | Trieu |
| 2004/0143284 A1 | 7/2004 | Chin |
| 2004/0143734 A1 | 7/2004 | Buer et al. |
| 2004/0147877 A1 | 7/2004 | Heuser |
| 2004/0147950 A1 | 7/2004 | Mueller et al. |
| 2004/0153156 A1 | 8/2004 | Cohen et al. |
| 2004/0158258 A1 | 8/2004 | Bonati et al. |
| 2004/0162617 A1 | 8/2004 | Zucherman et al. |
| 2004/0172134 A1 | 9/2004 | Berry |
| 2004/0186471 A1 | 9/2004 | Trieu |
| 2004/0186482 A1 | 9/2004 | Kolb et al. |
| 2004/0215343 A1 | 10/2004 | Hochschuler et al. |
| 2004/0215344 A1 | 10/2004 | Hochschuler et al. |
| 2004/0220580 A1 | 11/2004 | Johnson et al. |
| 2004/0225292 A1 | 11/2004 | Sasso et al. |
| 2004/0225361 A1 | 11/2004 | Glenn et al. |
| 2004/0243239 A1 | 12/2004 | Taylor |
| 2004/0249466 A1 | 12/2004 | Liu et al. |
| 2004/0254575 A1 | 12/2004 | Obenchain et al. |
| 2004/0266257 A1 | 12/2004 | Ries et al. |
| 2005/0033434 A1 | 2/2005 | Berry |
| 2005/0043796 A1 | 2/2005 | Grant et al. |
| 2005/0065610 A1 | 3/2005 | Pisharodi |
| 2005/0080443 A1 | 4/2005 | Fallin et al. |
| 2005/0090833 A1 | 4/2005 | Dipoto |
| 2005/0102202 A1 | 5/2005 | Linden et al. |
| 2005/0113927 A1 | 5/2005 | Malek |
| 2005/0118550 A1 | 6/2005 | Turri |
| 2005/0119657 A1 | 6/2005 | Goldsmith |
| 2005/0130929 A1 | 6/2005 | Boyd |
| 2005/0131406 A1 | 6/2005 | Reiley et al. |
| 2005/0131409 A1 | 6/2005 | Chervitz et al. |
| 2005/0131538 A1 | 6/2005 | Chervitz et al. |
| 2005/0137595 A1 | 6/2005 | Hoffmann et al. |
| 2005/0143734 A1 | 6/2005 | Cachia et al. |
| 2005/0149030 A1 | 7/2005 | Serhan et al. |
| 2005/0154467 A1 | 7/2005 | Peterman et al. |
| 2005/0165398 A1 | 7/2005 | Reiley |
| 2005/0171552 A1 | 8/2005 | Johnson et al. |
| 2005/0171608 A1 | 8/2005 | Peterman et al. |
| 2005/0171610 A1 | 8/2005 | Humphreys et al. |
| 2005/0182414 A1 | 8/2005 | Manzi et al. |
| 2005/0182418 A1 | 8/2005 | Boyd et al. |
| 2005/0187558 A1 | 8/2005 | Johnson et al. |
| 2005/0187559 A1 | 8/2005 | Raymond et al. |
| 2005/0203512 A1 | 9/2005 | Hawkins et al. |
| 2005/0216026 A1 | 9/2005 | Culbert |
| 2005/0251142 A1 | 11/2005 | Hoffmann et al. |
| 2005/0256525 A1 | 11/2005 | Culbert et al. |
| 2005/0278026 A1 | 12/2005 | Gordon et al. |
| 2005/0283238 A1 | 12/2005 | Reiley |
| 2006/0004326 A1 | 1/2006 | Collins et al. |
| 2006/0004457 A1 | 1/2006 | Collins et al. |
| 2006/0004458 A1 | 1/2006 | Collins et al. |
| 2006/0009778 A1 | 1/2006 | Collins et al. |
| 2006/0009779 A1 | 1/2006 | Collins et al. |
| 2006/0009851 A1 | 1/2006 | Collins et al. |
| 2006/0015105 A1 | 1/2006 | Warren et al. |
| 2006/0030872 A1 | 2/2006 | Culbert et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0041314 A1 | 2/2006 | Millard |
| 2006/0058790 A1 | 3/2006 | Carl et al. |
| 2006/0058807 A1 | 3/2006 | Landry et al. |
| 2006/0058880 A1 | 3/2006 | Wysocki et al. |
| 2006/0079908 A1 | 4/2006 | Lieberman |
| 2006/0084977 A1 | 4/2006 | Lieberman |
| 2006/0084988 A1 | 4/2006 | Kim |
| 2006/0085010 A1 | 4/2006 | Lieberman |
| 2006/0100707 A1 | 5/2006 | Stinson et al. |

(56) References Cited

U.S. PATENT DOCUMENTS

| | | |
|---|---|---|
| 2006/0106381 A1 | 5/2006 | Ferree et al. |
| 2006/0129244 A1 | 6/2006 | Ensign |
| 2006/0142765 A9 | 6/2006 | Dixon et al. |
| 2006/0142776 A1 | 6/2006 | Iwanari |
| 2006/0161166 A1 | 7/2006 | Johnson et al. |
| 2006/0178743 A1 | 8/2006 | Carter |
| 2006/0195103 A1 | 8/2006 | Padget et al. |
| 2006/0217711 A1 | 9/2006 | Stevens et al. |
| 2006/0229629 A1 | 10/2006 | Manzi et al. |
| 2006/0235403 A1 | 10/2006 | Blain |
| 2006/0235412 A1 | 10/2006 | Blain |
| 2006/0247634 A1 | 11/2006 | Warner et al. |
| 2006/0276899 A1 | 12/2006 | Zipnick et al. |
| 2006/0276901 A1 | 12/2006 | Zipnick et al. |
| 2006/0276902 A1 | 12/2006 | Zipnick et al. |
| 2006/0293662 A1 | 12/2006 | Boyer et al. |
| 2006/0293663 A1 | 12/2006 | Walkenhorst et al. |
| 2007/0010826 A1 | 1/2007 | Rhoda et al. |
| 2007/0032790 A1 | 2/2007 | Aschmann et al. |
| 2007/0055236 A1 | 3/2007 | Hudgins et al. |
| 2007/0067035 A1 | 3/2007 | Falahee |
| 2007/0073399 A1 | 3/2007 | Zipnick et al. |
| 2007/0118223 A1 | 5/2007 | Allard et al. |
| 2007/0123891 A1 | 5/2007 | Ries et al. |
| 2007/0123892 A1 | 5/2007 | Ries et al. |
| 2007/0129730 A1 | 6/2007 | Woods et al. |
| 2007/0162005 A1 | 7/2007 | Peterson et al. |
| 2007/0168036 A1 | 7/2007 | Ainsworth et al. |
| 2007/0203491 A1 | 8/2007 | Pasquet et al. |
| 2007/0233083 A1 | 10/2007 | Abdou |
| 2007/0233089 A1 | 10/2007 | Dipoto et al. |
| 2007/0270954 A1 | 11/2007 | Wu |
| 2007/0270968 A1 | 11/2007 | Baynham et al. |
| 2007/0282449 A1 | 12/2007 | De et al. |
| 2008/0058598 A1 | 3/2008 | Ries et al. |
| 2008/0077148 A1 | 3/2008 | Ries et al. |
| 2008/0082172 A1 | 4/2008 | Jackson |
| 2008/0108996 A1 | 5/2008 | Padget et al. |
| 2008/0147193 A1* | 6/2008 | Matthis ............... A61F 2/4465 623/17.16 |
| 2008/0255618 A1 | 10/2008 | Fisher et al. |
| 2008/0262619 A1 | 10/2008 | Ray |
| 2008/0287981 A1 | 11/2008 | Culbert et al. |
| 2008/0287997 A1 | 11/2008 | Altarac et al. |
| 2008/0300685 A1 | 12/2008 | Carls et al. |
| 2009/0069813 A1 | 3/2009 | Von et al. |
| 2009/0105745 A1 | 4/2009 | Culbert |
| 2009/0131986 A1 | 5/2009 | Lee et al. |
| 2009/0182429 A1 | 7/2009 | Humphreys et al. |
| 2009/0222100 A1* | 9/2009 | Cipoletti ............... A61F 2/447 623/17.16 |
| 2009/0275890 A1 | 11/2009 | Leibowitz et al. |
| 2009/0292361 A1 | 11/2009 | Lopez |
| 2010/0076492 A1 | 3/2010 | Warner et al. |
| 2010/0082109 A1 | 4/2010 | Greenhalgh et al. |
| 2010/0114147 A1 | 5/2010 | Biyani |
| 2010/0191336 A1 | 7/2010 | Greenhalgh |
| 2010/0211176 A1 | 8/2010 | Greenhalgh |
| 2010/0268231 A1 | 10/2010 | Kuslich et al. |
| 2010/0292700 A1 | 11/2010 | Ries |
| 2010/0292796 A1* | 11/2010 | Greenhalgh ....... A61B 17/8858 623/17.11 |
| 2010/0298938 A1 | 11/2010 | Humphreys et al. |
| 2010/0331891 A1 | 12/2010 | Culbert et al. |
| 2011/0040332 A1 | 2/2011 | Culbert et al. |
| 2011/0054538 A1 | 3/2011 | Zehavi et al. |
| 2011/0071527 A1 | 3/2011 | Nelson et al. |
| 2011/0098531 A1 | 4/2011 | To |
| 2011/0098628 A1 | 4/2011 | Yeung et al. |
| 2011/0130838 A1 | 6/2011 | Morgenstern Lopez |
| 2011/0153020 A1 | 6/2011 | Abdelgany et al. |
| 2011/0172774 A1 | 7/2011 | Varela |
| 2011/0238072 A1 | 9/2011 | Tyndall |
| 2011/0251690 A1* | 10/2011 | Berger ............... A61F 2/4425 623/17.16 |
| 2011/0282453 A1 | 11/2011 | Greenhalgh et al. |
| 2011/0307010 A1 | 12/2011 | Pradhan |
| 2011/0313465 A1 | 12/2011 | Warren et al. |
| 2011/0319997 A1* | 12/2011 | Glerum ................ A61F 2/447 623/17.15 |
| 2012/0006361 A1 | 1/2012 | Miyagi et al. |
| 2012/0059474 A1 | 3/2012 | Weiman |
| 2012/0059475 A1 | 3/2012 | Weiman |
| 2012/0150304 A1 | 6/2012 | Glerum et al. |
| 2012/0158147 A1 | 6/2012 | Glerum et al. |
| 2012/0158148 A1 | 6/2012 | Glerum et al. |
| 2012/0185049 A1 | 7/2012 | Varela |
| 2012/0191194 A1 | 7/2012 | Olmos |
| 2012/0197405 A1 | 8/2012 | Cuevas et al. |
| 2012/0203290 A1 | 8/2012 | Warren et al. |
| 2012/0203347 A1 | 8/2012 | Glerum et al. |
| 2012/0215262 A1 | 8/2012 | Culbert et al. |
| 2012/0226357 A1 | 9/2012 | Varela |
| 2012/0265309 A1* | 10/2012 | Glerum ................ A61F 2/447 623/17.16 |
| 2012/0290090 A1 | 11/2012 | Glerum et al. |
| 2012/0290097 A1 | 11/2012 | Cipoletti et al. |
| 2012/0323328 A1 | 12/2012 | Weiman |
| 2012/0330421 A1 | 12/2012 | Weiman |
| 2012/0330422 A1 | 12/2012 | Weiman |
| 2013/0023993 A1 | 1/2013 | Weiman |
| 2013/0023994 A1* | 1/2013 | Glerum ................ A61F 2/447 623/17.16 |
| 2013/0197642 A1* | 8/2013 | Ernst ................ A61F 2/442 623/17.16 |
| 2013/0197647 A1 | 8/2013 | Wolters et al. |
| 2014/0236296 A1* | 8/2014 | Wagner ................ A61F 2/447 623/17.15 |
| 2014/0277473 A1* | 9/2014 | Perrow ................ A61F 2/447 623/17.15 |

FOREIGN PATENT DOCUMENTS

| | | |
|---|---|---|
| DE | 3023353 A1 | 4/1981 |
| DE | 19832798 C1 | 11/1999 |
| DE | 20101793 U1 | 5/2001 |
| EP | 0077159 A1 | 4/1983 |
| EP | 0260044 A1 | 3/1988 |
| EP | 0433717 A1 | 6/1991 |
| EP | 0525352 A1 | 2/1993 |
| EP | 0611557 A2 | 8/1994 |
| EP | 0625336 A2 | 11/1994 |
| EP | 1046376 A1 | 10/2000 |
| EP | 0853929 B1 | 9/2002 |
| EP | 1374784 A1 | 1/2004 |
| EP | 1378205 A1 | 1/2004 |
| EP | 1845874 A1 | 10/2007 |
| EP | 2331023 A2 | 6/2011 |
| ES | 2361099 A1 | 6/2011 |
| FR | 2699065 A1 | 6/1994 |
| FR | 2728778 A1 | 7/1996 |
| FR | 2745709 A1 | 9/1997 |
| FR | 2800601 A1 | 5/2001 |
| FR | 2801189 A1 | 5/2001 |
| FR | 2808182 A1 | 11/2001 |
| GB | 2157788 A | 10/1985 |
| GB | 2173565 A | 10/1986 |
| JP | 64-052439 A | 2/1989 |
| JP | 06-500039 A | 1/1994 |
| JP | 06-319742 A | 11/1994 |
| JP | 07-502419 A | 3/1995 |
| JP | 07-184922 A | 7/1995 |
| JP | 10-085232 A | 4/1998 |
| JP | 11-089854 A | 4/1999 |
| JP | 2011-520580 A | 7/2011 |
| JP | 4988203 B2 | 8/2012 |
| JP | 5164571 B2 | 3/2013 |
| WO | 91/09572 A1 | 7/1991 |
| WO | 93/04652 A1 | 3/1993 |
| WO | 96/28100 A1 | 9/1996 |
| WO | 99/52478 A1 | 10/1999 |
| WO | 99/62417 A1 | 12/1999 |
| WO | 00/67652 A2 | 11/2000 |

(56) References Cited

FOREIGN PATENT DOCUMENTS

| WO | 00/76409 A1 | 12/2000 |
|---|---|---|
| WO | 01/12054 A2 | 2/2001 |
| WO | 01/80751 A1 | 11/2001 |
| WO | 02/43601 A2 | 6/2002 |
| WO | 03/21308 A2 | 3/2003 |
| WO | 03/43488 A2 | 5/2003 |
| WO | 2004/008949 A2 | 1/2004 |
| WO | 2004/064603 A2 | 8/2004 |
| WO | 2004/078220 A2 | 9/2004 |
| WO | 2004/078221 A2 | 9/2004 |
| WO | 2004/098453 A2 | 11/2004 |
| WO | 2005/112835 A2 | 12/2005 |
| WO | 2006/017507 A2 | 2/2006 |
| WO | 2006/063083 A1 | 6/2006 |
| WO | 2006/108067 A2 | 10/2006 |
| WO | 2007/119212 A2 | 10/2007 |
| WO | 2007/124130 A2 | 11/2007 |
| WO | 2008/044057 A1 | 4/2008 |
| WO | 2008/064842 A2 | 6/2008 |
| WO | 2008/070863 A2 | 6/2008 |
| WO | 2009/152919 A1 | 12/2009 |
| WO | 2010/136170 A1 | 12/2010 |
| WO | 2010/148112 A1 | 12/2010 |
| WO | 2011/079910 A2 | 7/2011 |
| WO | 2011/142761 A1 | 11/2011 |
| WO | 2011/150350 A1 | 12/2011 |

OTHER PUBLICATIONS

Apr. 19, 2007 Office Action for European Application No. 02 719 402.6 filed Mar. 29, 2002.
Apr. 19, 2007 Office Action Communication for Application No. 02719402.6 filed on Mar. 29, 2002.
Apr. 18, 2007 EPO Examination Report for App. No. 01 932 643.8.
Apr. 17, 2008 International Search Report and Written Opinion from corresponding PCT Application No. PCT/US07/09794 filed Apr. 20, 2007 in 8 pages.
Apr. 13, 2006 International Search Report for App. No. PCT/US2005/044321.
Alfen, et al., "Developments in the Area of Edoscopic Spine Surgery". European Musculoskeletal Review 2006, pp. 23-24. ThessysTM, Transforminal Endoscopic Spine System. Medical Solutions, ioimax®.
Gray's Anatomy, Crown Publishers, Inc., 1977, pp. 33-54.
Bone Fixation System, U.S. Appl. No. 09/558,057.
Zucherman, "A Multicenter, Prospective, Randomized Trial Evaluating the X STOP Interspinous Process Decompression System for the Treatment of Neurogenic Intermittent Claudication", Spine vol. 30, No. 12, pp. 1351-1358.
Vikram Talwar, "Insertion loads of the X STOP interspinous process distraction system designed to treat neurogenic intermittent claudication", Eur Spine J (2006) 15: pp. 908-912.
Sep. 7, 2009 Office Action for European Application No. 05 853 282.1filed Dec. 8, 2005.
Sep. 19, 2005 Office Action received in Australian Application No. 2002250488 filed Mar. 29, 2002.
Sep. 10, 2010 Supplementary European Search Report of European Application No. EP 0 674 0 578 filed on Apr. 4, 2006.
ProMapTM EMG Navigation Probe. Technical Brochure Spineology Inc., Dated May 2009.
Niosi, "Biomechanical characterization of the three-dimentional kinematic behaviour of the Dynesys dynamic stabilization system: an in vitro study", Eur Spine J (2006) 15: pp. 913-922.
Morgenstern R; Transforaminal Endoscopic Stenosis Surgery—A Comparative Study of Laser and Reamed Foraminoplasty.In: European Musculoskeletal Review, Issue 1, 2009.
Medco Forum, "Percutaneous Lumbar Fixation via PERPOS System From Interventional Spine". Oct. 2007, vol. 14, No. 49.
Medco Forum, "Percutaneous Lumbar Fixation Via PERPOS PLS System Interventional Spine". Sep. 2008, vol. 15, No. 37.

May 30, 2008 International Search Report & Written Opinion received in corresponding PCT Application No. PCT/US06/12728 in 9 pgs.
May 27, 2009 Office Action for Japanese Patent Application No. 2005-50552 filed on Jul. 18, 2003.
May 25, 2012 Office Action for EP Application No. 04716128.6.
May 25, 2009 Notice of Allowance received in Canadian Application No. 2,442,334 filed Mar. 29, 2002.
Mar. 31, 2010 Office Action for Japanese Patent Application No. 2005-505552 filed on Jul. 18, 2003.
Mar. 23, 2011 Office Action for Japanese Application No. 2005-505552 filed Jul. 18, 2003.
Mar. 14, 2012 Supplemental European Search Report for Application No. Ep 05 77 7628.
Mar. 12, 2009 International Preliminary Report on Patentability, received in corresponding PCT Application No. PCT/US2007/009794 filed Apr. 20, 2007, in 5 pages.
Manal Siddiqui, "The Positional Magnetic Resonance Imaging Changes in the Lumbar Spine Following Insertion of a Novel Interspinous Process Distraction Device", Spine vol. 30, No. 23, pp. 2677-2682.
Mahar, et al. Biomechanical Comparison of a Novel Percutaneous Transfacet Device and a Traditional Posterior System for Single Level Fusion. Journal of Spinal Disorders & Techniques, Dec. 2006, vol. 19 No. 8, pp. 591-594.
King, "Internal Fixation for Lumbosacral Fusion", The Journal of Bone and Joint Surgery. J Bone Joint Surg Am. 1948; 30:560-578.
Kambin, et al; Percutaneous Lateral Discectomy of the Lumbar Spine: A Preliminary Report; Clin. Orthop.; 1983; 174: 127-132.
Jun. 25, 2012 International Search Report and Written Opinion for PCT Application No. PCT/US2012/02811 0, the PCT counterpart of the present application.
Jun. 22, 2006 European Search Report for Application No. 02719402.6 filed Mar. 29, 2002.
Jun. 18, 2009 Preliminary Report on Patentability received in co-pending PCT Application No. PCT/US2007/086866 filed Dec. 7, 2007.
Jun. 18, 2007 Notice of Acceptance received in Australian Application No. 2002250488 filed Mar. 29, 2002
Jul. 7, 2008 International Search Report and Written Opinion received in co-pending PCT Application No. PCT/US2007/086866 filed Dec. 7, 2007.
Jul. 7, 2008 International Search Report and Written Opinion received in co-pending PCT Application No. PCT/US2005/027431 filed Aug. 2, 2005.
Jul. 5, 2011 Office Action (Rejection Notice dated Jul. 13, 2011) for Japanese Application No. 2007-545602.
Jul. 3, 2008 Office Action received for Canadian Application No. 2,442,334 filed Mar. 29, 2002.
Jul. 2, 2009 Office Action for U.S. Appl. No. 11/308,767, filed May 1, 2006.
Jan. 9, 2008 Supplemental Partial European Search Report received in corresponding European Application No. 0 471 618.
Jan. 27, 2011 Office Action for Australian Application No. 2005314079 filed Dec. 8, 2005.
Jan. 26, 2005 International Search Report and Written Opinion received in corresponding PCT App. No. PCT/US04/06129, 13 pages.
Iprenburg, et al., "Transforaminal Endoscopic Surgery in Lumbar Disc Herniation in an Economic Crisis—The TESSYS Method". US Musculoskeletal, 2008 pp. 47-49.
Fuchs, "The Use of an Interspinous Implant in Conjunction With a Graded Facetectomy Procedure", Spine vol. 30, No. 11, pp. 1266-1272.
Feb. 7, 2011 Office Action for Japanese Application No. 2007-524917 filed Aug. 2, 2005.
Feb. 24, 2012 Office Action for Japanese Application No. 2007-524917 filed Aug. 2, 2005.
Chin, "Early Results of the Triage Medical Percutaneous Transfacet Pedicular BONE-LOK Compression Device for Lumbar Fusion".
Brooks et al., Efficacy of Supplemental Posterior Transfacet Pedicle Device Fixation in the Setting of One- or Two-Level Anterior Lumbar Interbody Fusion.

(56) References Cited

OTHER PUBLICATIONS

Brochure for PERPOS PLS System Surgical Technique by Interventional Spine.
Aug. 4, 2009 Extended European Search Report received in European Application No. 09164698.4, 5 pages.
Aug. 4, 2005 EPO Examination Report for App. No. 01 932 643.8.
Apr. 6, 2007 Office Action received in Chinese Application No. 02810329.7 filed Mar. 29, 2002.
Apr. 3, 2009 Extended European Search Report received in European Application No. 09152476.9 in 5 pages.
Apr. 29, 2008 Notice for Preliminary Rejection in Korean Application No. 2003-7012847 filed Mar. 29, 2002.
Apr. 28, 2011 Supplementary European Search Report for Application No. EP 07 75 5880 filed on Apr. 20, 2007.
Apr. 22, 2008 Supplemental ISR rec'd in corresponding EP Application No. 04716129.4
Apr. 22, 2004 International Search Report for App. No. PCT/US03/23645 filed Jul. 18, 2003.
Apr. 20, 2010 International Search Report and Written Opinion in co-pending PCT Application No. PCT/IB2009/005972 in 19 pages \* cited by examiner

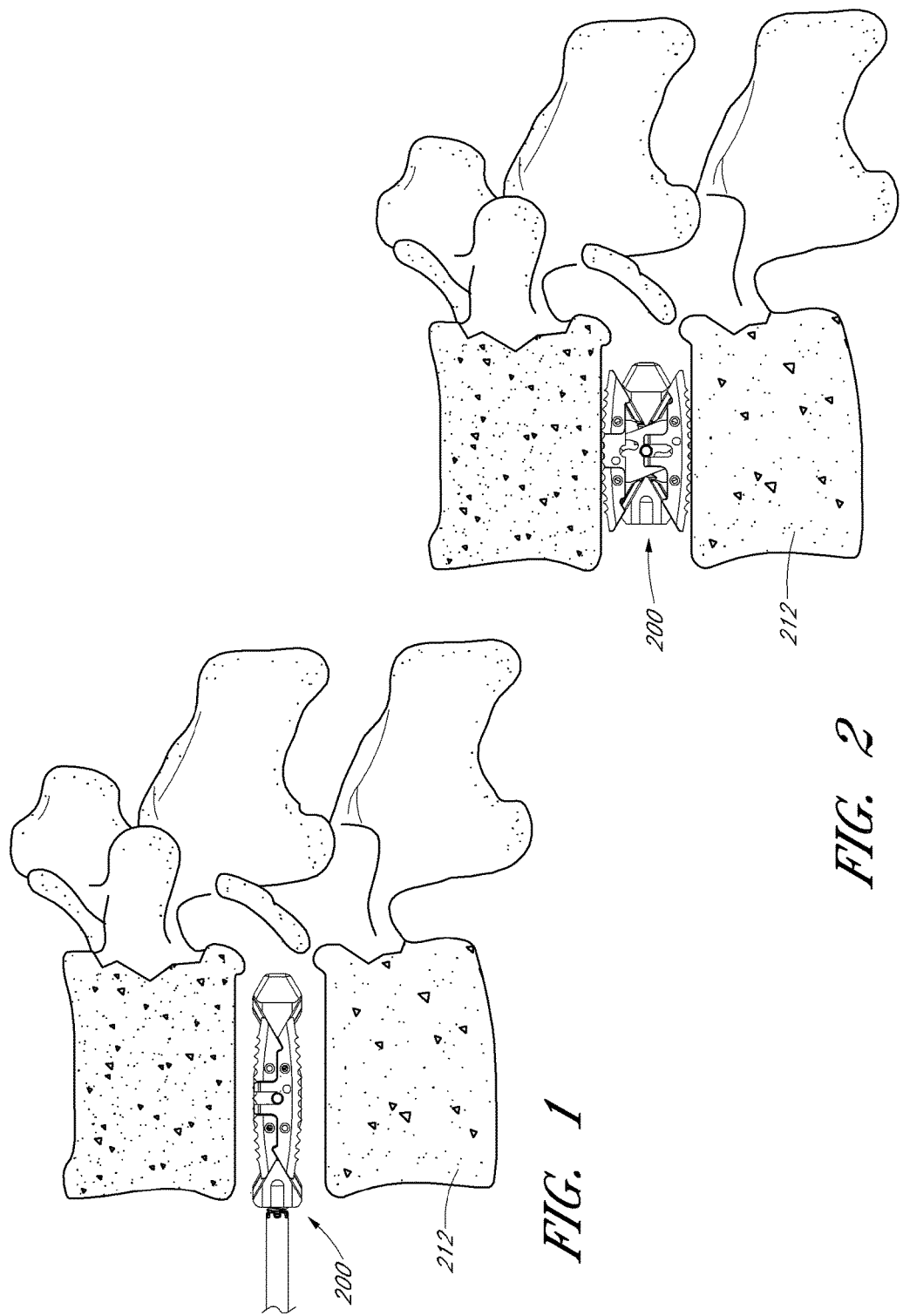

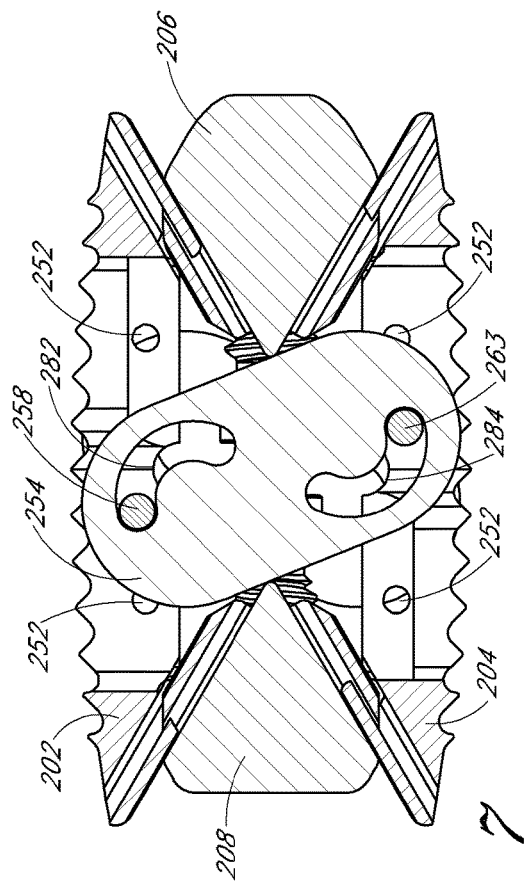
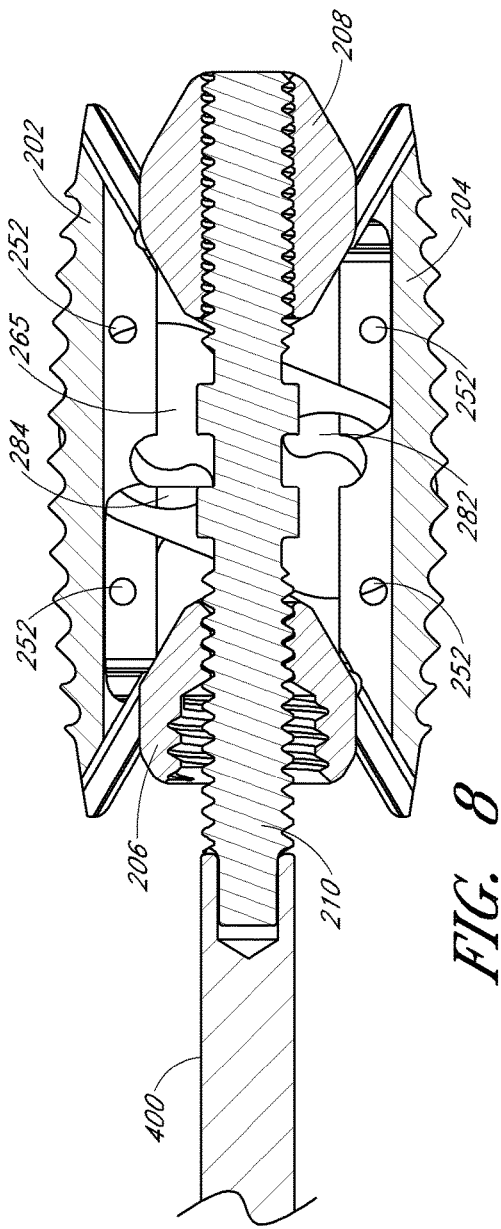
FIG. 7
FIG. 8

INTERVERTEBRAL IMPLANT

CROSS-REFERENCE TO RELATED APPLICATIONS

This application is a continuation of U.S. application Ser. No. 13/789,507, filed Mar. 7, 2013. The entire disclosure of this prior application is hereby incorporated by reference in its entirety and should be considered a part of this specification.

BACKGROUND

Field

The present invention relates to medical devices and, more particularly, to an intervertebral implant.

Description of the Related Art

The human spine is a flexible weight bearing column formed from a plurality of bones called vertebrae. There are thirty three vertebrae, which can be grouped into one of five regions (cervical, thoracic, lumbar, sacral, and coccygeal). Moving down the spine, there are generally seven cervical vertebra, twelve thoracic vertebra, five lumbar vertebra, five sacral vertebra, and four coccygeal vertebra. The vertebra of the cervical, thoracic, and lumbar regions of the spine are typically separate throughout the life of an individual. In contrast, the vertebra of the sacral and coccygeal regions in an adult are fused to form two bones, the five sacral vertebra which form the sacrum and the four coccygeal vertebra which form the coccyx.

In general, each vertebra contains an anterior, solid segment or body and a posterior segment or arch. The arch is generally formed of two pedicles and two laminae, supporting seven processes—four articular, two transverse, and one spinous. There are exceptions to these general characteristics of a vertebra. For example, the first cervical vertebra (atlas vertebra) has neither a body nor spinous process. In addition, the second cervical vertebra (axis vertebra) has an odontoid process, which is a strong, prominent process, shaped like a tooth, rising perpendicularly from the upper surface of the body of the axis vertebra. Further details regarding the construction of the spine may be found in such common references as Gray's Anatomy, Crown Publishers, Inc., 1977, pp. 33-54, which is herein incorporated by reference.

The human vertebrae and associated connective elements are subjected to a variety of diseases and conditions which cause pain and disability. Among these diseases and conditions are spondylosis, spondylolisthesis, vertebral instability, spinal stenosis and degenerated, herniated, or degenerated and herniated intervertebral discs. Additionally, the vertebrae and associated connective elements are subject to injuries, including fractures and torn ligaments and surgical manipulations, including laminectomies.

The pain and disability related to the diseases and conditions often result from the displacement of all or part of a vertebra from the remainder of the vertebral column. Over the past two decades, a variety of methods have been developed to restore the displaced vertebra to their normal position and to fix them within the vertebral column. Spinal fusion is one such method. In spinal fusion, one or more of the vertebra of the spine are united together ("fused") so that motion no longer occurs between them. Thus, spinal fusion is the process by which the damaged disc is replaced and the spacing between the vertebrae is restored, thereby eliminating the instability and removing the pressure on neurological elements that cause pain.

Spinal fusion can be accomplished by providing an intervertebral implant between adjacent vertebrae to recreate the natural intervertebral spacing between adjacent vertebrae. Once the implant is inserted into the intervertebral space, osteogenic substances, such as autogenous bone graft or bone allograft, can be strategically implanted adjacent the implant to prompt bone in-growth in the intervertebral space. The bone ingrowth promotes long-term fixation of the adjacent vertebrae. Various posterior fixation devices (e.g., fixation rods, screws etc.) can also be utilize to provide additional stabilization during the fusion process.

Recently, intervertebral implants have been developed that allow the surgeon to adjust the height of the intervertebral implant. This provides an ability to intra-operatively tailor the intervertebral implant height to match the natural spacing between the vertebrae. This reduces the number of sizes that the hospital must keep on hand to match the variable anatomy of the patients.

In many of these adjustable intervertebral implants, the height of the intervertebral implant is adjusted by expanding an actuation mechanism through rotation of a member of the actuation mechanism. In some intervertebral implants, the actuation mechanism is a screw or threaded portion that is rotated in order to cause opposing plates of the implant to move apart. In other implants, the actuation mechanism is a helical body that is counter-rotated to cause the body to increase in diameter and expand thereby.

Furthermore, notwithstanding the variety of efforts in the prior art described above, these intervertebral implants and techniques are associated with another disadvantage. In particular, these techniques typically involve an open surgical procedure, which results higher cost, lengthy in-patient hospital stays and the pain associated with open procedures.

Therefore, there remains a need in the art for an improved intervertebral implant. Preferably, the implant is implantable through a minimally invasive procedure. Further, such devices are preferably easy to implant and deploy in such a narrow space and opening while providing adjustability and responsiveness to the clinician.

SUMMARY OF THE INVENTION

Certain aspects of this disclosure are directed toward an adjustable spinal fusion intervertebral implant. The implant can include upper and lower body portions each having proximal and distal surfaces at proximal and distal ends thereof. The proximal and distal surfaces of the upper and lower body portions can generally face each other. The implant can include a proximal wedge member disposed at the proximal ends of the respective ones of the upper and lower body portions, and a distal wedge member disposed at the distal ends of the respective ones of the upper and lower body portions. The implant can include first and second linkages each connected to the upper and lower body portions. The implant can include an actuator shaft received between the upper and lower body portions. The actuator shaft can extend intermediate the distal and proximal wedge members. Rotation of the actuator shaft can cause the distal and proximal wedge members to be drawn together such that longitudinal movement of the distal wedge member against the distal surfaces and the longitudinal movement of the proximal wedge member against the proximal surfaces causes separation of the upper and lower body portions. The implant features described in the specification can be included in any of the implant embodiments.

In some embodiments, The proximal surfaces of the respective ones of the upper and lower body portions each define a proximal slot therein, and distal surfaces of the respective ones of the upper and lower body portions each define a distal slot therein. In certain aspects, the slots of the proximal and distal surfaces of the upper and lower body portions are generally dove-tailed. In certain aspects, the proximal wedge member and the distal wedge member can each include upper and lower guide members extending at least partially into the respective ones of the proximal and distal slots of the upper and lower body portions with at least a portion of the proximal wedge member and the distal wedge member contacting the proximal and distal surfaces of the upper and lower body portions. The guide members of the proximal and distal wedge members can be generally dovetailed.

In some embodiments, each of the upper and lower body portions can include a first side portion having an extending portion and a second side portion having a receiving portion. The first side portion of the upper body portion can be configured to mate with the second side portion of the lower body portion. The second side portion of the upper body portion can be configured to mate with the first side portion of the lower body portion. In certain aspects, the first and second side portions of the upper body portion can be configured to disengage from the first and second side portions of the lower body portion when the implant is in an expanded state.

In some embodiments, the proximal and distal surfaces of the upper and lower body portions can be sloped.

In some embodiments, the upper and lower body portions comprise generally arcuate respective upper and lower exterior engagement surfaces.

In some embodiments, the proximal wedge member can include an anti-rotational element. The anti-rotational engagement can be configured to engage an implant tool to prevent rotation of the implant when the actuator shaft is rotated relative to the implant. In certain aspects, the anti-rotational element can include a pair of apertures extending into the proximal wedge member.

In some embodiments, each of the first and second linkages can include at least one cam path. In certain aspects, a pin can extend from the at least one cam path to one of the upper and lower body portions.

In some embodiments, a length of the implant varies from about 45 mm to about 54 mm and/or a height of the implant varies from about 6.5 mm to about 12 mm during the separation of the upper and lower body portions. In certain aspects, the length of the implant varies from about 21 mm to about 31 mm during the separation of the upper and lower body portions.

In some embodiments, the upper and lower body portions can be coated with a bio-active coating, including, but not limited to, a hydroxyapatite coating, a titanium plasma spray, a resorbable blast media coating, or composite coatings.

Certain aspects of this disclosure are directed toward a method of manufacturing an adjustable spinal fusion intervertebral implant. The method can include extending an actuator shaft from a proximal wedge member to a distal wedge member. The method can include engaging the proximal and distal wedge members with each of the upper and lower body portions. The method can include connecting first and second linkages to each of the upper and lower body portions. The method of manufacturing steps described in the specification can be included in any of the embodiments discussed herein.

In some embodiments, extending the actuator shaft from the proximal wedge member to the distal wedge member can include inserting the actuator shaft through a central aperture of the proximal wedge member and through a central aperture of the distal wedge member.

In some embodiments, engaging the proximal and distal wedge members with each of the upper and lower body portions can include extending upper and lower guide members of the proximal and distal wedge members at least partially into respective ones of proximal and distal slots of the upper and lower body portions.

In some embodiments, the method can include engaging a first side portion of the upper body portion and a second side portion of the lower body portion. The first side portion can have an extending portion, and the second side portion can have a receiving portion. The receiving portion can be configured to receive the extending portion.

In some embodiments, engaging the first and second linkages with each of the upper and lower body portions can include extending a pin from a cam path of one of the first and second linkages to one of the upper and lower body portions.

In some embodiments, the method can include shot-peening the upper and lower body portions.

In some embodiments, the method can include coating the upper and lower body portions with a bio-active coating, including, but not limited to, a hydroxyapatite coating, a titanium plasma spray, a resorbable blast media coating, or composite coatings.

Certain aspects of this disclosure are directed toward a method of implanting an expandable intervertebral implant. The method can include positioning the implant between two vertebral bodies. The method can include rotating a screw mechanism of the implant to cause proximal and distal wedge members to converge toward each other and engage respective ones of proximal and distal surfaces of upper and lower body portions of the implant. The method can include separating the upper and lower body portions to cause the implant to expand. In certain aspects, separating the upper and lower body portions can cause first and second linkages to rotate from a first configuration to a second configuration. The method of use steps discussed in the specification can be included in any of the embodiments described herein.

In some embodiments, a height of the first and second linkages can be greater in the second configuration than in the first configuration.

In some embodiments, the method can include moving one or more pins along a respective cam path of one of the first and second linkages to cause the first and second linkages to rotate from the first configuration to the second configuration.

For purposes of summarizing the disclosure, certain aspects, advantages and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

FIG. 1 is a side view of an intervertebral implant in an unexpanded state while positioned intermediate adjacent vertebrae, according to an embodiment.

FIG. 2 is a side view of the intervertebral implant shown in FIG. 1 in an expanded state.

FIG. 7 is a side cross-sectional view of the intervertebral implant shown in FIG. 4 in an expanded state, the cross-sectional view is taken along line 7-7 of FIG. 4.

FIG. 8 is a side cross-sectional view of the intervertebral implant shown in FIG. 4 in an expanded state, the cross-sectional view is taken along line 8-8 of FIG. 4.

DETAILED DESCRIPTION

Figure 3:
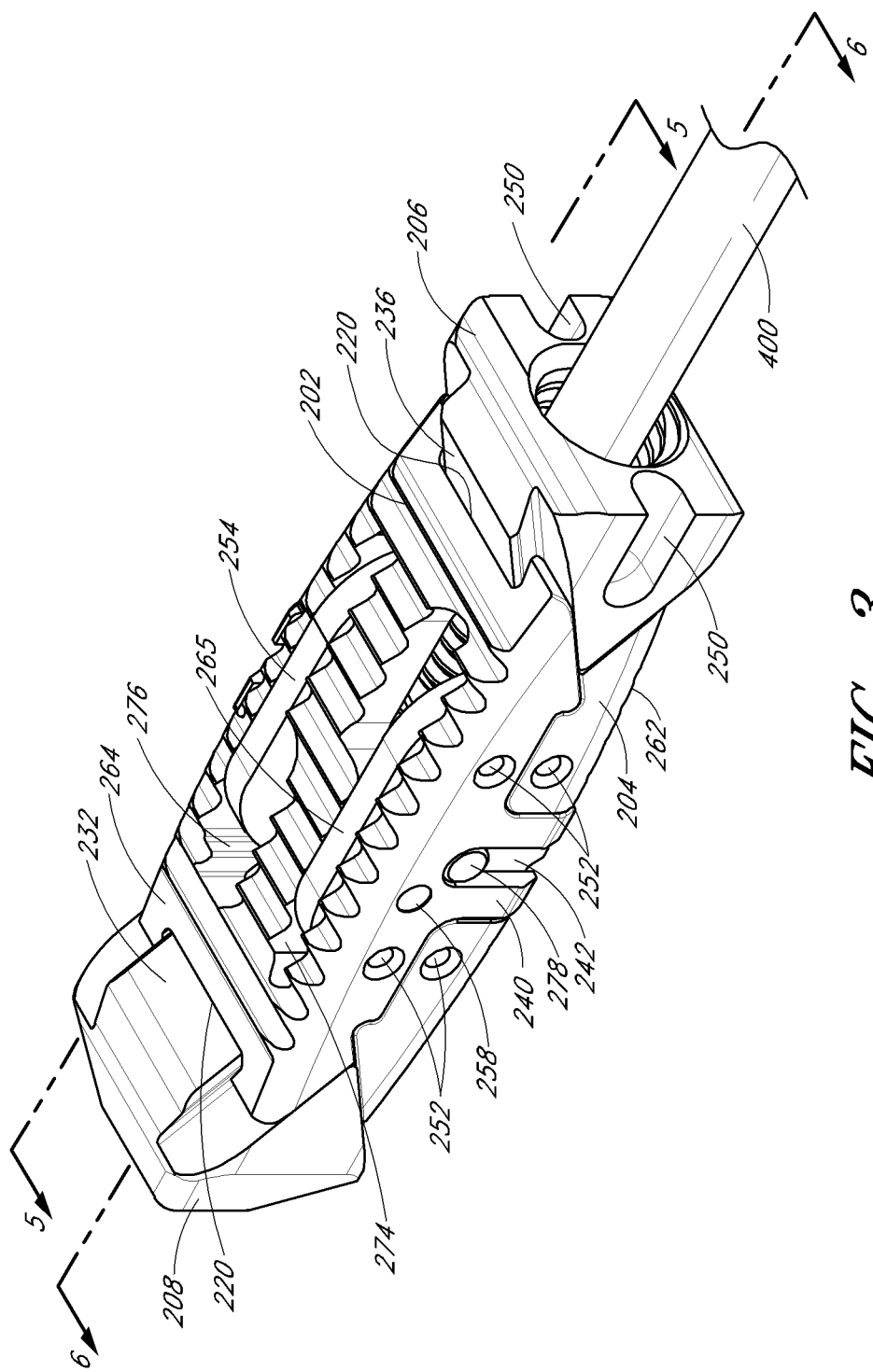
FIG. 3 is a perspective view of the intervertebral implant shown in FIG. 1 in an unexpanded state.

In accordance with certain embodiments disclosed herein, an improved intervertebral implant is provided that allows the clinician to insert the intervertebral implant through a minimally invasive procedure. For example, one or more intervertebral implants can be inserted percutaneously to reduce trauma to the patient and thereby enhance recovery and improve overall results of the surgery.

An intervertebral implant can include a plurality of body sections that are selectively separable and expandable upon contraction of a centrally disposed actuator. The actuator can be utilized to contract against faces of the body sections to cause the expansion thereof. The implant can also be configured such that the actuator provides for both the expansion and contraction of the body sections. The actuator can comprise an interaction between the body sections and another element, an action performed by another element, or a combination of interactions between various elements of the implant and its body sections. Further, the implant can be configured to allow either rough or fine incremental adjustments in the expansion of the implant.

The embodiments disclosed herein are discussed in the context of an intervertebral implant and spinal fusion because of the applicability and usefulness in such a field. As such, various embodiments can be used to properly space adjacent vertebrae in situations where a disc has ruptured or otherwise been damaged. As also disclosed herein, embodiments can also be used as vertebral body replacements. Thus, "adjacent" vertebrae can include those originally separated only by a disc or those that are separated by intermediate vertebra and discs. Such embodiments can therefore tend to recreate proper disc height and spinal curvature as required in order to restore normal anatomical locations and distances. However, it is contemplated that the teachings and embodiments disclosed herein can be beneficially implemented in a variety of other operational settings, for spinal surgery and otherwise.

For example, the implant disclosed herein can also be used as a vertebral body replacement. In such a use, the implant could be used as a replacement for a lumbar vertebra, such as one of the L1-L5 vertebrae. Thus, the implant could be appropriately sized and configured to be used intermediate adjacent vertebrae, or to entirely replace a damaged vertebra.

It is contemplated that the implant can be used as an interbody or intervertebral device or can be used to replace a vertebral body entirely. The implant can also be used in vertebral body compression fractures. Further, the implant can be used as a tool to expand an intervertebral space or bone in order to fill the space or bone with a cement; in such cases, the implant can be removed or left in once the cement is placed. Furthermore, the implant can also be used as a tool to pre-dilate the disc space. In some embodiments, the implant can be removed once the disc space is dilated, and a different implant (expandable or non-expandable) can then be implanted in the dilated disc space. The implant can also be introduced into the disc space anteriorly in an anterior lumbar interbody fusion (ALIF) procedure, posterior in an posterior lumbar interbody fusion (PILF) or posterior lateral interbody fusion, from extreme lateral position in an extreme lateral interbody fusion procedure (XLIF) or direct lateral interbody fusion (DLIF), from a far lateral position in a transforaminal lumbar interbody fusion (TLIF), to name a few. In other arrangements, the implant can be inserted through the Kambin triangle or be inserted through the Kambin triangle after the Kambin triangle has been enlarged via removing bone (e.g., techniques such as PerX360° System™ sold by Intervention Spine®). Although the implant is primarily described herein as being used to expand in a vertical direction, it can also be implanted to expand in a horizontal direction in order to increase stability and/or increase surface area between adjacent vertebral bodies.

Therefore, it is contemplated that a number of advantages can be realized utilizing various embodiments disclosed herein. For example, as will be apparent from the disclosure, no external distraction of the spine is necessary. Further, no distraction device is required in order to install various embodiments disclosed herein. In this regard, embodiments of the implant can enable sufficient distraction of adjacent vertebra in order to properly restore disc height or to use the implant as a vertebral body replacement. Thus, normal anatomical locations, positions, and distances can be restored and preserved utilizing many of the embodiments disclosed herein.

Referring to FIG. 1, there is illustrated a side view of an embodiment of a intervertebral implant 200 in an unexpanded state while positioned generally between adjacent vertebrae of the lumbar portion of the spine 212. FIG. 2 illustrates the intervertebral implant 200 in an expanded state, thereby supporting the vertebrae in a desired orientation and spacing in preparation for spinal fusion. As is known in the art, spinal fusion is the process by which the adjacent vertebrae of the spine are united together ("fused") so that motion no longer occurs between the vertebrae. Thus, the intervertebral implant 200 can be used to provide the proper spacing two vertebrae to each other pending the healing of a fusion. See also U.S. Pat. No. 7,824,429, filed Jul. 18, 2003, the entirety of the disclosure of which is hereby incorporated by reference.

In certain embodiment, the implant can be installed in an operation that generally entails the following procedures. The damaged disc or vertebra can be decompressed, such as by distracting. The subject portion (or entire) disc or vertebra can then be removed. The adjacent vertebrae can be prepared by scraping the exposed adjacent portion or plates thereof (typically to facilitate bleeding and circulation in the area). Typically, most of the nucleus of the disc is removed and the annulus of the disc is thinned out. Although individual circumstances may vary, it may be unusual to remove all of the annulus or to perform a complete diskectomy. The implant can then be installed. In some embodiments, distraction of the disc may not be a separate step from placement of the implant; thus, distraction can be accomplished and can occur during placement of the implant. Finally, after implantation of the implant, osteogenic substances, such as autogenous bone graft, bone allograft, autograft foam, or bone morphogenic protein (BMP) can be strategically implanted adjacent the implant to prompt bone in-growth in the intervertebral space. In this regard, as the implant is expanded, the spaces within the implant can be backfilled; otherwise, the implant can be pre-packed with biologics.

The intervertebral implant is often used in combination with posterior and/or anterior fixation devices (e.g., rods, plates, screws, etc. that span two or more vertebrae) to limit movement during the fusion process. U.S. Pat. No. 7,824, 429 discloses a particularly advantageous posterior fixation device and method which secures two adjacent vertebra to each other in a trans-laminar, trans-facet or facet-pedicle (e.g., the Boucher technique) application using fixation screws.

It should also be appreciated that in FIGS. 1 and 2 only one intervertebral implant 200 is shown positioned between the vertebrae 212. However, two, three, or more implants 200 can be inserted into the space between the vertebrae 212. Further, other devices, such as bone screws, can be used on the vertebrae as desired. For example, in a spinal fusion procedure, it is contemplated that one or more implants 200 can be used in conjunction with one or more bone screws and/or dynamic stabilization devices, such as those disclosed in the above-mentioned U.S. Pat. No. 7,824,429, filed Jul. 18, 2003.

In certain embodiments, the implant 200 can be used in combination with a dynamic stabilization devices such as those disclosed in U.S. Pat. No. 7,648,523, filed Feb. 11, 2005; U.S. Pat. No. 6,951,561, filed on May 6, 2004; U.S. Pat. No. 7,998,176, filed on Jun. 6, 2008; and U.S. Pat. No. 7,824,429, filed Jul. 18, 2003; the entireties of the disclosures of which are hereby incorporated by reference. In this manner, the implant 200 can be used to maintain height between vertebral bodies while the dynamic stabilization device provides limits in one or more degrees of movement.

Figure 4:
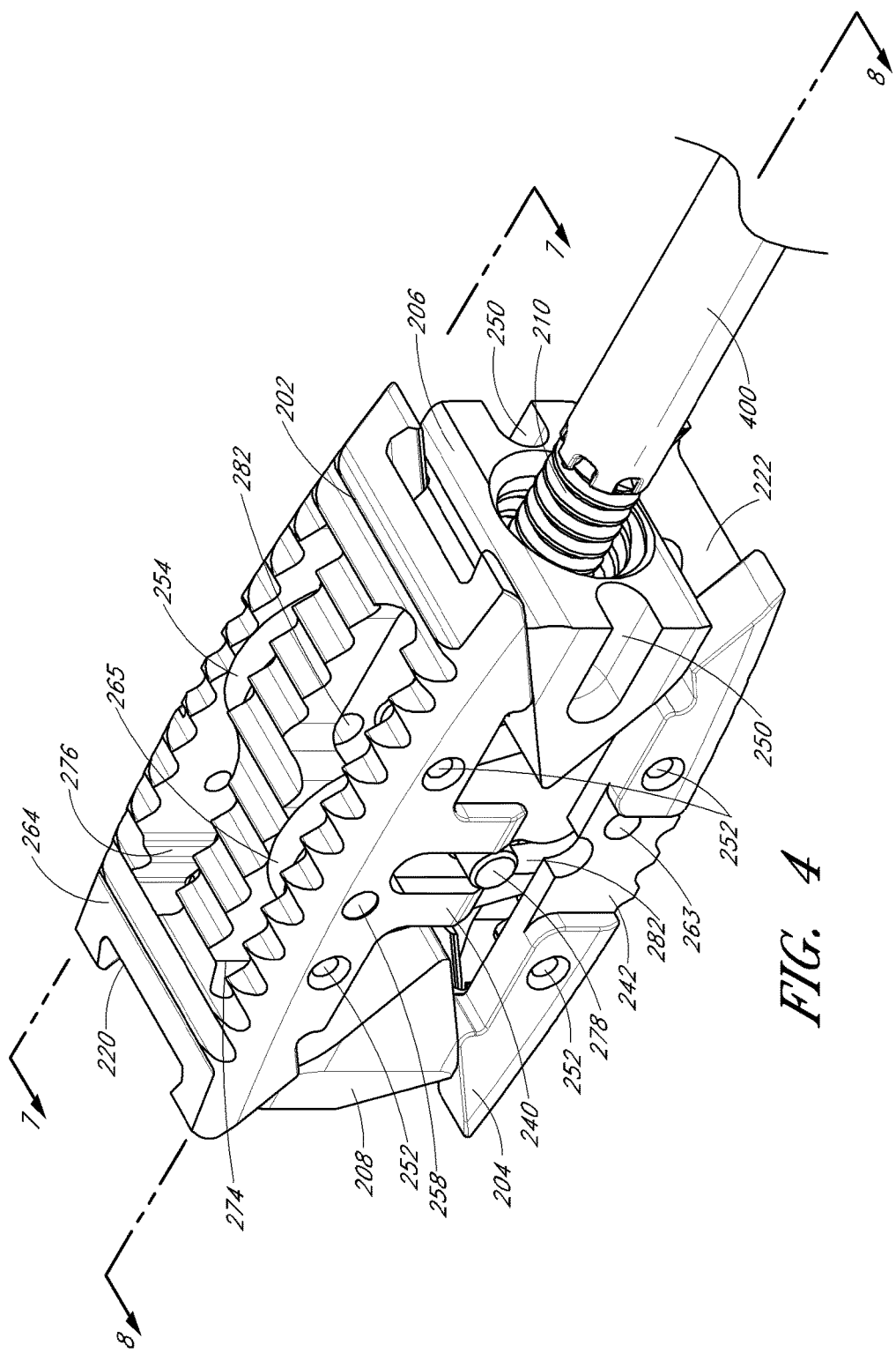
FIG. 4 is a perspective view of the intervertebral implant shown in FIG. 1 in an expanded state.
Figure 5:
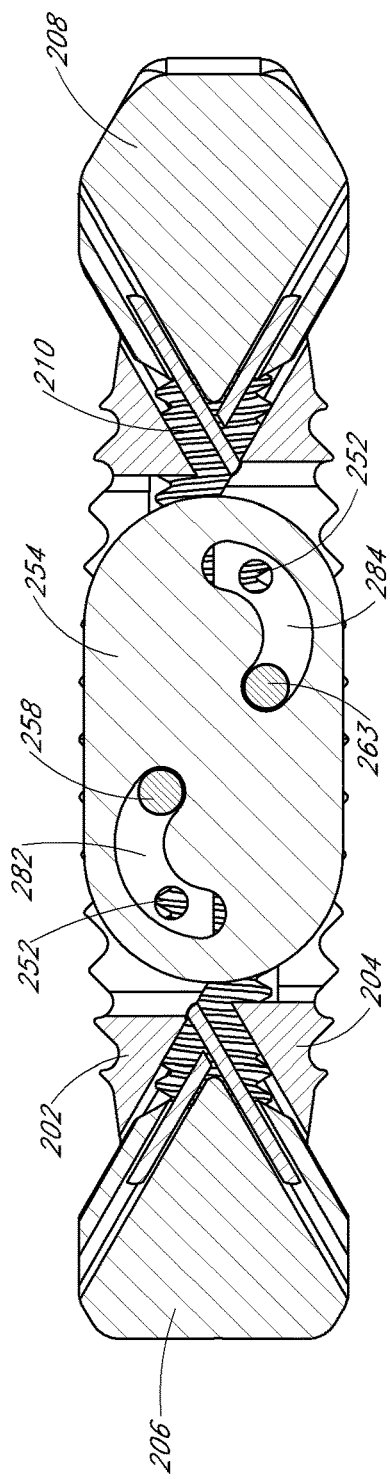
FIG. 5 is a side cross sectional view of the intervertebral implant shown in FIG. 3 in an unexpanded state, the cross sectional view is taken along line 5-5 of FIG. 3.
Figure 6:
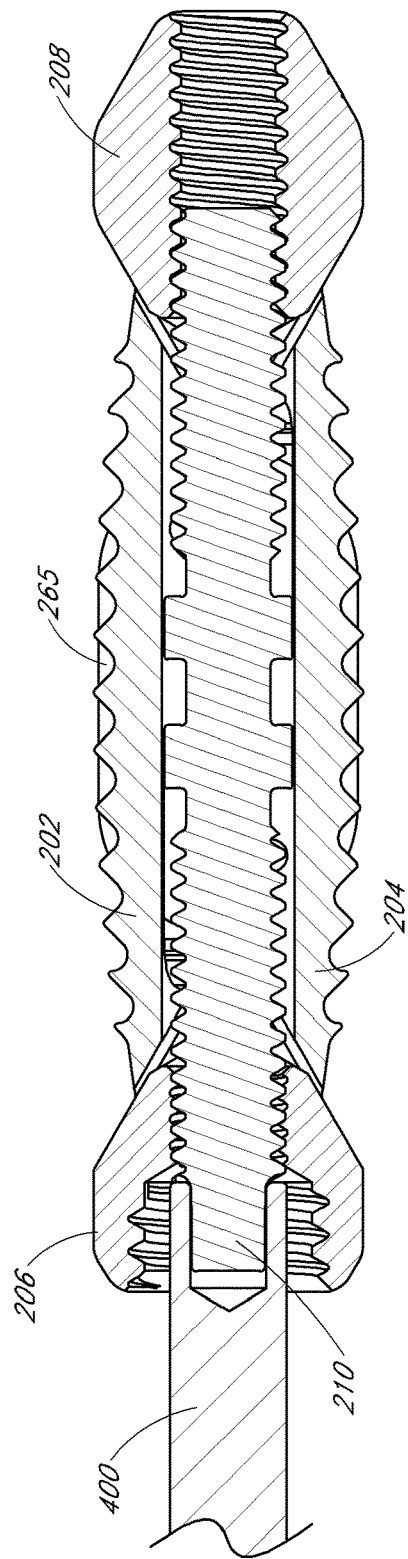
FIG. 6 is a side cross sectional view of the intervertebral implant shown in FIG. 3 in an unexpanded state, the cross sectional view is taken along line 6-6 of FIG. 3.

FIG. 3 is a perspective view of an intervertebral implant 200 in an unexpanded state, and FIGS. 5 and 6 illustrate cross-sections of the intervertebral implant 200 in the unexpanded state. The implant 200 can comprise upper and lower body portions 202, 204, proximal and distal wedge members 206, 208, first and second linkages 254, 265, and an actuator shaft 210. In the unexpanded state, the upper and lower body portions 202, 204 can be generally abutting with a height of the implant 200 being minimized. However, the implant 200 can be expanded, as shown in FIG. 4, to increase the height of the implant 200 when implanted into the intervertebral space of the spine. FIGS. 7 and 8 illustrate cross-sections of the intervertebral implant 200 in the expanded state.

It is contemplated that the actuator shaft 210 can be rotated to cause the proximal and distal wedge members to move toward each other, thus causing the upper and lower body portions 202, 204 to be separated. In some embodiments, the implant 200 can include one or more linkages configured to connect the upper and lower body portions 202, 204 when the implant 200 is in an expanded state. For example, as shown in FIGS. 3 and 4, the implant 200 can include first and second linkages 254, 265. The linkages 254, 265 can be configured to move between a first configuration (shown in FIG. 5) and a second configuration (shown in FIG. 7).

Each of the intervertebral implant components will be described in further detail below in reference to FIGS. 9-21.

In some embodiments, the height of the implant 200 can be or vary within a range from at least about 6 mm to less than or equal to about 15 mm, and more preferably, from about 6.5 mm to about 12 mm. The width of the implant can be at least about 7 mm and/or less than or equal to about 18 mm, and preferably approximately 9 mm or 18 mm. Thus, the implant 200 can have a preferred aspect ratio of between approximately 6:18 and 15:7, and preferably approximately between 6.5:9 and 12:9, or between 6.5:18 and 12:18.

The length of the implant 200 can be or vary within a range from at least 18 mm to less than or equal to about 54 mm. In certain aspects, the length of the implant 200 can be or vary within a range from least about 18 mm to less than or equal to about 35 mm, and preferably from about 25 mm to about 31 mm. In certain aspects, the length of the implant 200 can be or vary within a range from least about 45 mm to less than or equal to about 54 mm. In some embodiments, the implant can have a greater length in the unexpanded state than in the expanded state. It is contemplated that various modifications to the dimension disclosed herein can be made by one of skill and the mentioned dimensions shall not be construed as limiting.

The intervertebral implant components can be manufactured in accordance with any of a variety of techniques which are well known in the art, using any of a variety of medical-grade construction materials. For example, the upper and lower body portions 202, 204, the actuator shaft 210, and other components can be injection-molded from a variety of medical-grade polymers including high or other density polyethylene, PEEK™ polymers, nylon and polypropylene.

The intervertebral implant 200 components can be molded, formed or machined from biocompatible metals such as Nitinol, stainless steel, titanium, and others known in the art. Non-metal materials such as plastics, PEEK™ polymers, and rubbers can also be used. Further, the implant components can be made of combinations of PEEK™ polymers and metals. In some embodiments, the intervertebral implant components can be injection-molded from a bioabsorbable material, to eliminate the need for a post-healing removal step.

The intervertebral implant components may be coated with or contain one or more bioactive substances, such as antibiotics, chemotherapeutic substances, angiogenic growth factors, substances for accelerating the healing of the wound, growth hormones, anti-thrombogenic agents, bone growth accelerators or agents, and the like. Such bioactive implants may be desirable because they contribute to the healing of the injury in addition to providing mechanical support. For example, in some embodiments, the upper and lower body portions 202, 204 can be coated with a bio-active coating, including, but not limited, to a hydroxyapatite coating, a titanium plasma spray, a resorbable blast media coating, or composite coatings. The upper and lower body portions 202, 204 can be coated after the implant is fully assembled, such that other components exposed along the upper and lower surfaces of the implant can also be coated with hydroxyapatite.

In some embodiments, the intervertebral implant components can be surface treated to increase the strength of the components. For example, the intervertebral implant components can be sand blasted, shot peened, laser peened, or otherwise treated to increase strength.

In addition, the intervertebral implant components may be provided with any of a variety of structural modifications to accomplish various objectives, such as osteoincorporation, or more rapid or uniform absorption into the body. For example, osteoincorporation may be enhanced by providing a micropitted or otherwise textured surface on the intervertebral implant components. Alternatively, capillary pathways may be provided throughout the intervertebral implant, such as by manufacturing the intervertebral implant components from an open cell foam material, which produces tortuous pathways through the device. This construction increases the surface area of the device which is exposed to body fluids, thereby generally increasing the absorption rate. Capillary pathways may alternatively be provided by laser drilling or other technique, which will be understood by those of skill in the art in view of the disclosure herein. Additionally, apertures can be provided in the implant to facilitate packing of biologics into the implant, backfilling, and/or osseointegration of the implant. In general, the extent to which the intervertebral implant can be permeated by capillary pathways or open cell foam passageways may be determined by balancing the desired structural integrity of the device with the desired reabsorption time, taking into account the particular strength and absorption characteristics of the desired polymer.

The implant 200 can be at least partially radiolucent, which radiolucency can allow a doctor to perceive the degree of bone growth around and through the implant. The individual components of the implant 200 can be fabricated of such materials based on needed structural, biological and optical properties.

The intervertebral implant may be sterilized by any of the well-known sterilization techniques, depending on the type of material. Suitable sterilization techniques include heat sterilization, ultrasonic sterilization, radiation sterilization, such as cobalt irradiation or electron beams, ethylene oxide sterilization, and the like.

Figure 9:
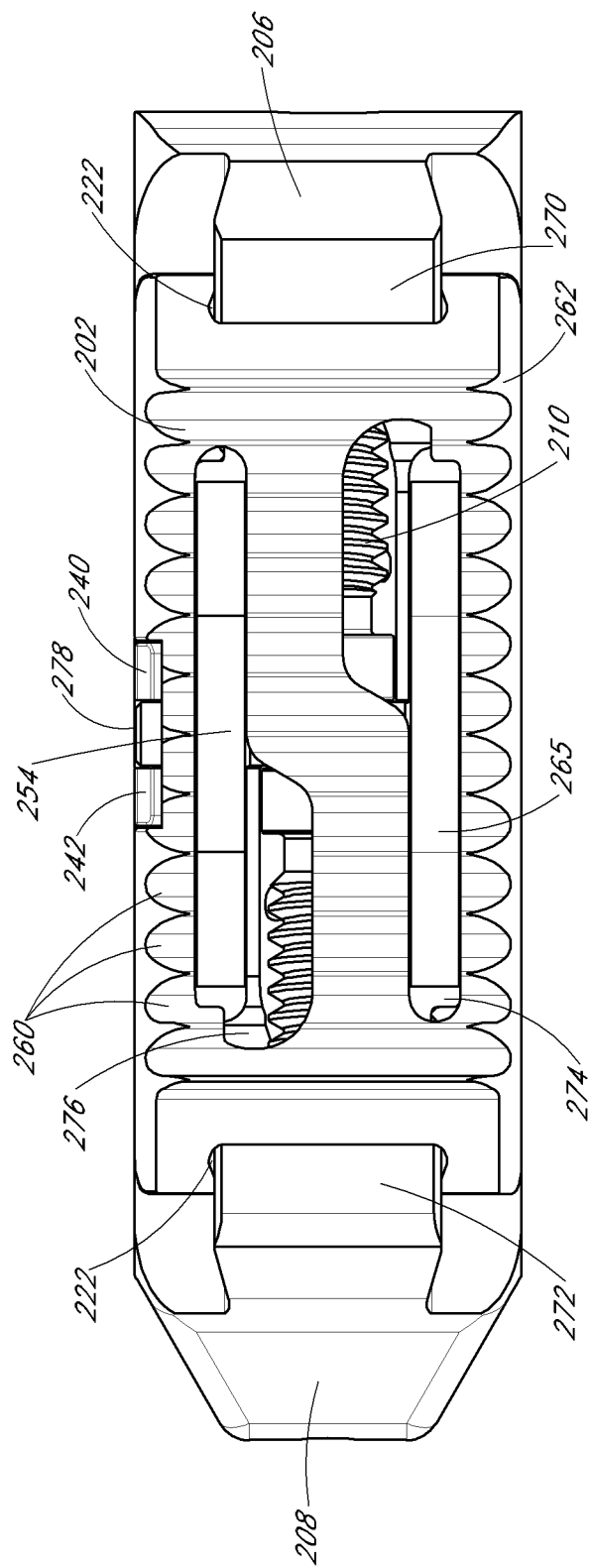
FIG. 9 is a bottom view of the intervertebral implant shown in FIG. 1 in an unexpanded state.
Figure 13:
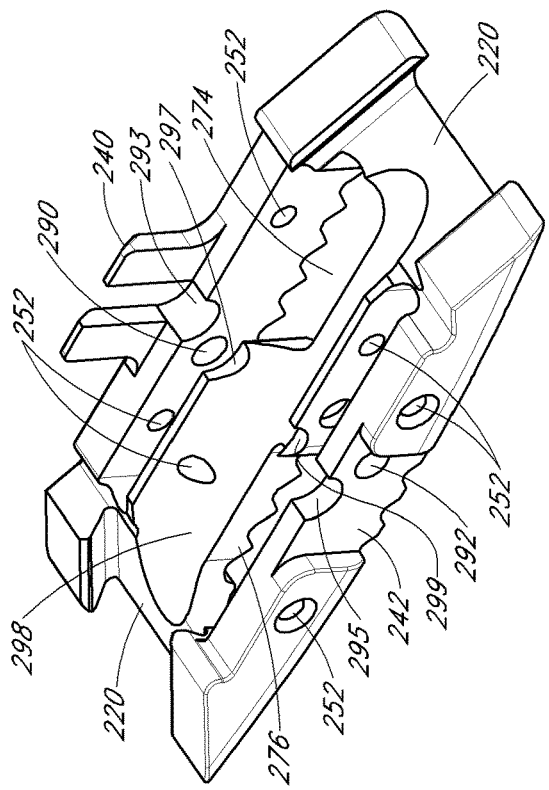
FIG. 13 is a bottom perspective view of the upper body portion of the intervertebral implant shown in FIG. 1.

FIG. 9 is a bottom view of the implant 200 shown in FIG. 3. As shown therein, each of the upper and lower body portions 202, 204 can also include one or more openings 274, 276 for receiving the first and second linkages 254, 265 and/or receiving graft material or other bioactive substances. The openings 274, 276 can be disposed on either side of a central receptacle 298 (FIG. 13).

In some embodiments, the two openings 274, 276 can be similarly shaped. For example, as shown in FIG. 9, each opening 274, 276 can include a first elongate portion having a width and a second portion having a width greater than the first elongate portion width. As shown in FIG. 9, at least a part of the actuator shaft 210 is visible through the second portion of each opening 274, 276. The second opening 276 can be disposed at a 180 degree angle from the first opening 274 and/or horizontally displaced from the first opening 274.

In certain variants, the openings 274, 276 can be single elongate portions through which the first and second linkages 254, 265 extend. Although not shown in the FIGS., the upper and lower body portions 202, 204 can include additional openings for receiving graft material or other bioactive substances. Each of the openings can be shaped similarly or differently. The additional openings can be vertically and/or horizontally displaced from each other along the upper and body portions 202, 204. The additional opens can be aligned with a longitudinal axis of the implant 200 or positioned off-center. One or more of the openings can be generally rounded, including, but not limited to, a generally elliptical shape, or include a light-bulb shape. The width of one or more of the openings can vary across a length of the opening.

Figure 12:
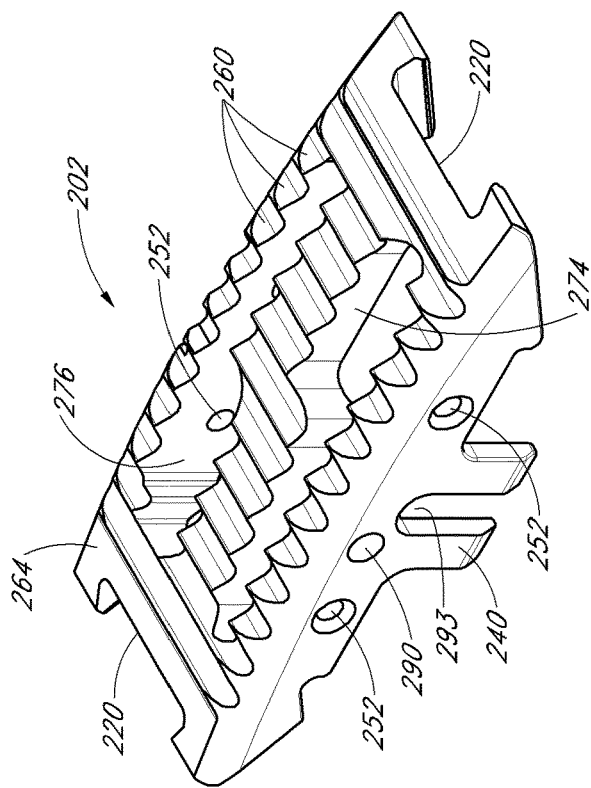
FIG. 12 is a top perspective view of an upper body portion of the intervertebral implant shown in FIG. 1.

In some embodiments, the implant 200 can comprise one or more protrusions 260 on a bottom surface 262 of the lower body portion 204. As shown in FIG. 12, the upper body portion 204 can also define a top surface having one or more protrusions 260 thereon. The protrusions 260 can allow the implant 200 to engage the adjacent vertebrae when the implant 200 is expanded to ensure that the implant 200 maintains a desired position in the intervertebral space.

The protrusions 260 can be configured in various patterns. As shown, the protrusions 260 can be formed from grooves extending widthwise along the bottom surface 262 of the implant 200 (also shown extending from a top surface 264 of the upper body portion 202 of the implant 200). The protrusions 260 can become increasingly narrow and pointed toward their apex. However, it is contemplated that the protrusions 260 can be one or more raised points, cross-wise ridges, or the like.

In FIG. 9, the implant 200 is illustrated in the unexpanded state with each of the respective slots 222 of the lower body portion 204 and lower guide members 270, 272 of the respective ones of the proximal and distal wedge members 206, 208. In some embodiments, as shown in FIGS. 12-13, the slots and guide members can be configured to incorporate a generally dovetail shape. Thus, once a given guide member is slid into engagement with a slot, the guide member can only slide longitudinally within the slot and not vertically from the slot. This arrangement can ensure that the proximal and distal wedge members 206, 208 are securely engaged with the upper and lower body portions 202, 204.

Figure 10:
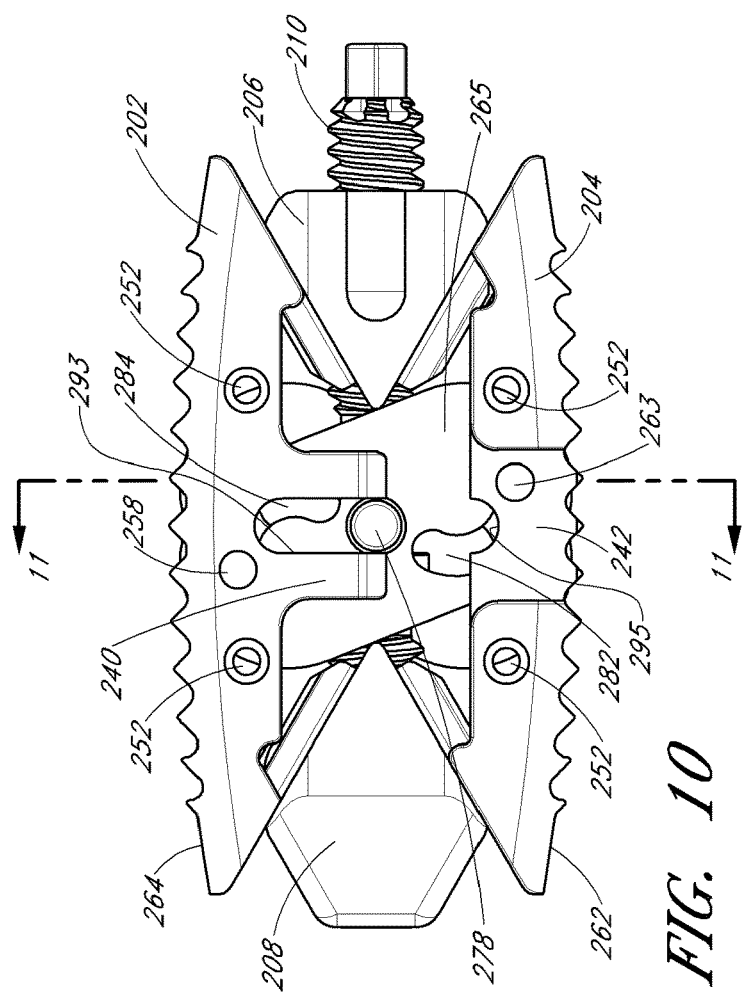
FIG. 10 is a side view of the intervertebral implant shown in FIG. 1 in an expanded state.

In FIG. 10, a side view of the embodiment of the implant 200 in the expanded state illustrates the angular relationship of the proximal and distal wedge members 206, 208 and the upper and lower body portions 202, 204. As mentioned above, the dovetail shape of the slots and guide members ensures that for each given slot and guide member, a given wedge member is generally interlocked with the give slot to only provide one degree of freedom of movement of the guide member, and thus the wedge member, in the longitudinal direction of the given slot.

Accordingly, in such an embodiment, the wedge members 206, 208 may not be separable from the implant when the implant 200 is in the unexpanded state (as shown in FIG. 3) due to the geometric constraints of the angular orientation of the slots and guide members with the actuator shaft inhibiting longitudinal relative movement of the wedge members 206, 208 relative to the upper and lower body portions 202,

204. Such a configuration ensures that the implant 200 is stable and structurally sound when in the unexpanded state or during expansion thereof, thus facilitating insertion and deployment of the implant 200.

Such an embodiment of the implant 200 can therefore be assembled by placing or engaging the wedge members 206, 208 with the actuator shaft 210, moving the wedge members 206, 208 axially together, and inserting the upper guide members 230, 232 into the slots 220 of the upper body portion 202 and the lower guide members 270, 272 into the slots 222 of the lower body portion 204. The wedge members 206, 208 can then be moved apart, which movement can cause the guide members and slots to engage and bring the upper and lower body portions toward each other. The implant 200 can then be prepared for insertion and deployment by reducing the implant 200 to the unexpanded state.

Referring again to FIG. 10, the implant 200 can define generally convex top and bottom surfaces 264, 262. This shape can be configured to generally match the concavity of adjacent vertebral bodies.

FIGS. 12-13 illustrate perspective views of the upper body portion 202 of the implant 200, according to an embodiment. These FIGS. provide additional clarity as to the configuration of the slots 220 and illustrate a first and second side portions 240, 242 of the upper body portion 202. The upper and lower body portions 202, 204 can also define a central receptacle 298 wherein the actuator shaft can be received, and two openings 274, 276 for receiving the first and second linkages 254, 265. Although the FIGS. illustrate the actuator shaft 210 disposed along a central receptacle 298 of the upper and lower body portions 202, 204, in certain variants, the actuator shaft 210 can be disposed off-center. This may be useful to provide a continuous graft channel along a central portion of the implant, from the top surface of the implant to the bottom surface of the implant.

It is contemplated that some embodiments of the implant 200 can be configured such that the upper and lower body portions 202, 204 each include side portions (shown as first side portion 240 and second side portion 242 of the upper body portion 202) to facilitate the alignment, interconnection, and stability of the components of the implant 200. The first and second side portions 240, 242 can be configured to have complementary structures that enable the upper and lower body portions 202, 204 to move in a vertical direction an maintain alignment in a horizontal direction. For example, as shown in FIGS. 12-13, the first side portion 240 can include an extending portion and the second side portion 242 can include a receiving portion for receiving the extending portion of the first side portion 240. As shown in FIG. 10, the first and second side portions 240, 242 of the upper body portion 202 can be configured to disengage from the first and second side portions 240, 242 of the lower body portion 202 when the implant 200 is in the expanded state.

FIG. 9 illustrates a bottom view of the profile of an embodiment of the first side portion 240 and the second side portion 242. As shown in FIG. 9, having a pair of each of first and second side portions 240, 242 can ensure that the upper and lower body portions 202, 204 do not translate relative to each other, thus further ensuring the stability of the implant 200.

In some embodiments, the implant 200 can be configured to include one or more apertures 252 to facilitate osseointegration of the implant 200 within the intervertebral space. As mentioned above, the implant 200 may contain one or more bioactive substances, such as antibiotics, chemotherapeutic substances, angiogenic growth factors, substances for accelerating the healing of the wound, growth hormones, anti-thrombogenic agents, bone growth accelerators or agents, and the like. Indeed, various biologics can be used with the implant 200 and can be inserted into the disc space or inserted along with the implant 200. The apertures 252 can facilitate circulation and bone growth throughout the intervertebral space and through the implant 200. In such implementations, the apertures 252 can thereby allow bone growth through the implant 200 and integration of the implant 200 with the surrounding materials.

Figure 14:
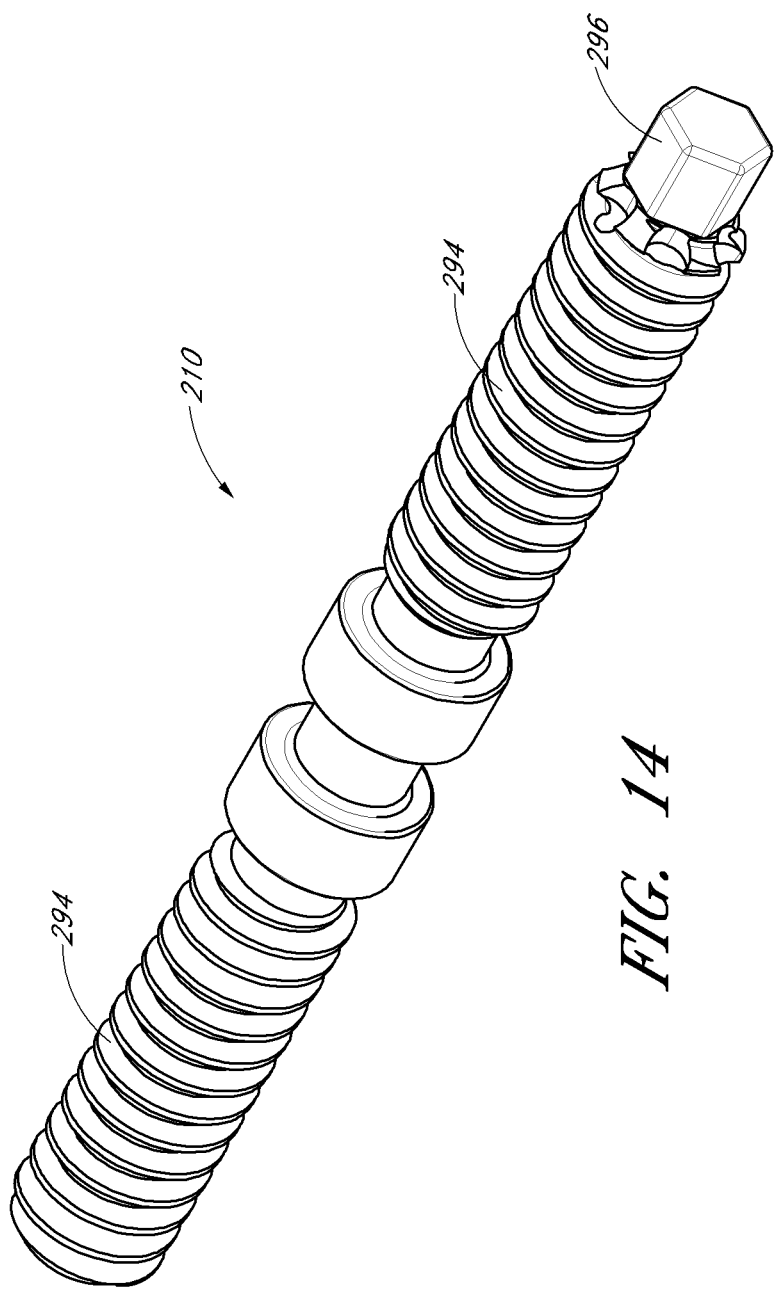
FIG. 14 is a perspective view of an actuator shaft of the intervertebral implant shown in FIG. 1.

As shown in FIG. 14, the actuator shaft 210 can have at least one thread 294 disposed along at least a portion thereof, if not along the entire length thereof. The actuator shaft 210 can be threadably and/or freely attached to one or both of the proximal and distal wedge members 206, 208. The actuator shaft 210 can also be configured such that a proximal portion of the actuator shaft 210 can be removed after the implant 200 has been expanded in order to eliminate any proximal protrusion of the actuator shaft 210. Although, the present embodiment is illustrated using this mode of expansion, it is contemplated that other modes of expansion (e.g., one way-ratchet type mechanism) can be combined with or interchanged herewith.

The threads can be configured to be left hand threads at a distal end of the actuator shaft 210 and right hand threads at a proximal other end of the actuator shaft 210 for engaging the respective ones of the distal and proximal wedge members 208, 206. Accordingly, upon rotation of the actuator shaft 210, the wedge members 206, 208 can be caused to move toward or away from each other to facilitate expansion or contraction of the implant 200.

In some embodiments, the actuator shaft 210 can facilitate expansion of the implant 200 through rotation, longitudinal contract of the pin, or other mechanisms. The actuator shaft 210 can include threads that threadably engage at least one of the proximal and distal wedge members 206, 208. The actuator shaft 210 can also facilitate expansion through longitudinal contraction of the actuator shaft as proximal and distal collars disposed on inner and outer sleeves move closer to each other to in turn move the proximal and distal wedge members closer together. It is contemplated that in certain variants, at least a portion of the actuator shaft can be axially fixed relative to one of the proximal and distal wedge members 206, 208 with the actuator shaft being operative to move the other one of the proximal and distal wedge members 206, 208 via rotational movement or longitudinal contraction of the pin.

In some embodiments, wherein the actuator shaft 210 is threaded, it is contemplated that the actuator shaft 210 can be configured to bring the proximal and distal wedge members closer together at different rates. In such embodiments, the implant 200 could be expanded to a V-configuration or wedged shape. For example, the actuator shaft 210 can comprise a variable pitch thread that causes longitudinal advancement of the distal and proximal wedge members at different rates. The advancement of one of the wedge members at a faster rate than the other could cause one end of the implant to expand more rapidly and therefore have a different height that the other end. Such a configuration can be advantageous depending on the intervertebral geometry and circumstantial needs.

The actuator shaft 210 can be utilized to provide a stabilizing axial force to the proximal and distal wedge members 206, 208 in order to maintain the expansion of the implant 200. However, it is also contemplated that other features can be incorporated into such an embodiment to facilitate the maintenance of the expansion. In this regard, although the axial force provided by the actuator shaft 210 can tend to maintain the position and stability of the proximal and distal wedge members 206, 208, additional features can be employed to ensure the strength and stability of the implant 200 when in its expanded state. For example, the proximal and distal wedge members 206, 208 can include ribbed engagement surfaces (not shown). The use of the ribbed engagement surfaces can permit one-way, ratchet type longitudinal movement of proximal and distal wedge members 206, 208 relative to the upper and lower body portions 202, 204 in order to maintain the upper and lower body portions at a given separation distance. Various other features that can be used to facilitate the expansion of two body portions of an intervertebral implant are disclosed in U.S. Pat. No. 8,105,382, filed Dec. 7, 2007, the entirety of which is hereby incorporated by reference.

The actuator shaft 210 can be cannulated and/or include one or more apertures. The one or more apertures and/or cannula can provide access to an internal portion of the implant, so bone graft or other bioactive materials described herein can be directly injected into the implant to promote fusion.

In accordance with an embodiment, the actuator shaft 210 can also comprise a tool engagement section 296. The tool engagement section 296 can be configured as a to be engaged by a tool 400. The tool engagement section 296 can be shaped as a polygon, such as a hex shape to facilitate the transfer of torque to the actuator shaft 210 from the tool 400. For example, the tool 400 can include a distal engagement member 430 being configured to engage a proximal end of the actuator shaft 210 of the implant 200 for rotating the actuator shaft 210 to thereby expand the implant from an unexpanded state to and expanded state.

The proximal end of the actuator shaft can also include a number of tool engagement features configured to engage with a number of corresponding engagement features at a distal end of the tool 400 (shown in FIG. 4). These tool engagement features can be configured to increase torque strength and facilitate rotation of the actuator shaft. As shown in FIG. 14, the tool engagement features can take the form of one or more grooves or indentations. The number of tool engagement features can equal the number of faces on the tool engagement section. For example, the actuator shaft 210 can include six tool engagement features. The tool engagement features can be disposed at a proximal end of the actuator shaft 210, between the threaded portion 294 and the tool engagement section 296. In certain aspects, the tool engagement features can surround a base of the tool engagement section 296. FIG. 4 illustrates the corresponding engagement features of the tool 400. The corresponding features can take the form of protrusions, nubs, fingers, or otherwise, at the distal end of the tool 400.

Figure 16:
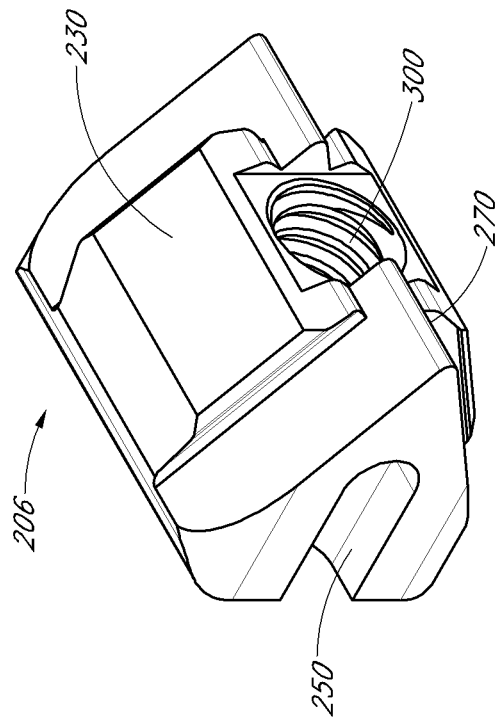
FIG. 16 is a rear perspective view of the proximal wedge member of the intervertebral implant shown in FIG. 1.
Figure 15:
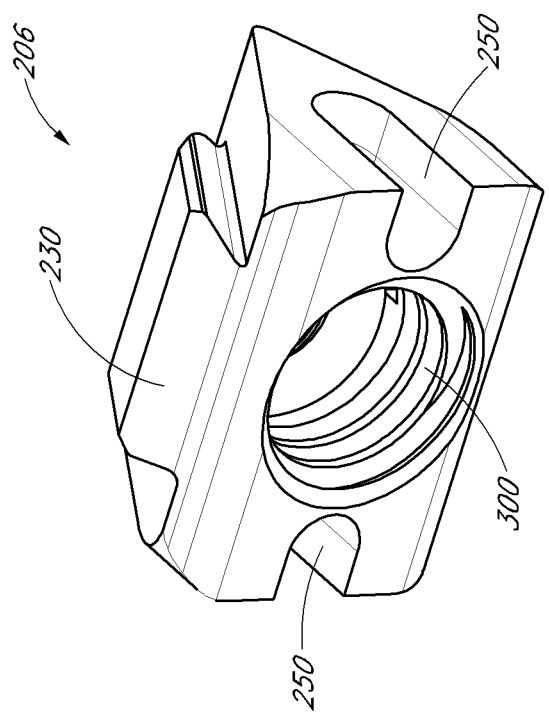
FIG. 15 is a front perspective view of a proximal wedge member of the intervertebral implant shown in FIG. 1.

FIG. 15-16 illustrate perspective views of the proximal wedge member 206 of the implant 200. The proximal wedge member 206 can include one or more anti-torque structures 250. Further, the guide members 230, 270 are also illustrated. The proximal wedge member 206 can comprise a central aperture 300 wherethrough an actuator shaft can be received. When actuator shaft 210 is used in an embodiment, the central aperture 300 can be threaded to correspond to the threads 294 of the actuator shaft 210. In other embodiments, the actuator shaft can engage other portions of the wedge member 206 for causing expansion or contraction thereof.

Figure 18:
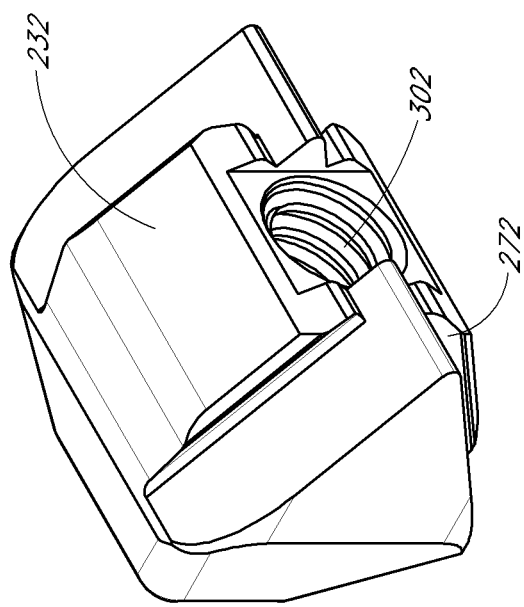
FIG. 18 is a rear perspective view of the distal wedge member of the intervertebral implant shown in FIG. 1.
Figure 17:
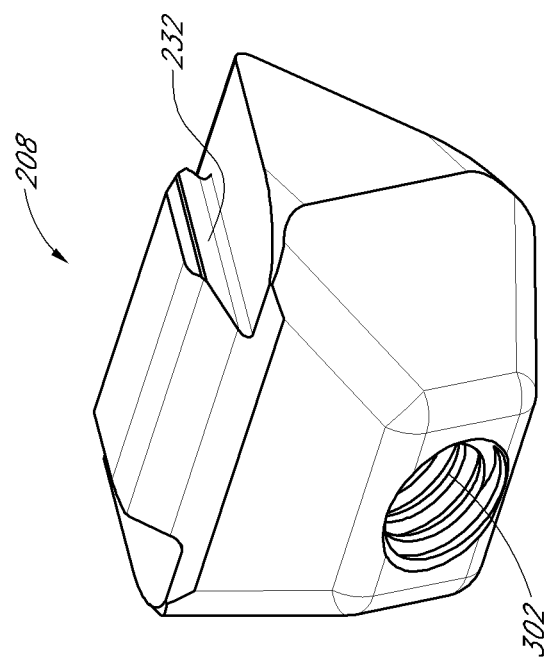
FIG. 17 is a front perspective view of a distal wedge member of the intervertebral implant shown in FIG. 1.

In some embodiments, the implant 200 can be configured such that the proximal and distal wedge members 206, 208 are interlinked with the upper and lower body portions 202, 204 to improve the stability and alignment of the implant 200. For example, the upper and lower body portions 202, 204 can be configured to include slots (slot 220 is shown in FIG. 3, and slots 220, 222 are shown in FIG. 4). The proximal and distal wedge members 206, 208 can be configured to include at least one guide member (an upper guide member 230 of the proximal wedge member 206 is shown in FIGS. 15-16 and an upper guide member 232 of the distal wedge member 208 is shown in FIGS. 17-18) that at least partially extends into a respective slot 220, 222 of the upper and lower body portions 202, 204. The arrangement of the slots and the guide members can enhance the structural stability and alignment of the implant 200.

In some embodiments, the implant 200 can be configured to include anti-torque structures 250. The anti-torque structures 250 can interact with at least a portion of a deployment tool during deployment of the implant to ensure that the implant maintains its desired orientation. For example, when the implant 200 is being deployed and a rotational force is exerted on the actuator shaft 210, the anti-torque structures 250 can be engaged by a non-rotating structure of the deployment tool to maintain the rotational orientation of the implant 200 while the actuator shaft 210 is rotated. The anti-torque structures 250 can comprise one or more inwardly extending holes or indentations on the proximal wedge member 206, which are shown as a pair of holes in FIGS. 3-4. However, the anti-torque structures 250 can also comprise one or more outwardly extending structures.

The tool 400 can also include an anti-torque component to engage one or more anti-torque structures 250 of the implant 200. The anti-torque component can include one or more protrusions that engage the anti-torque structures 250 to prevent movement of the implant 200 when a rotational force is applied to the actuator shaft 210 via the tool 400. Other deployment methods can also be used, such as those disclosed in U.S. Pat. No. 8,105,382.

FIG. 17-18 illustrate perspective views of the distal wedge member 208 of the implant 200. As similarly discussed above with respect to the proximal wedge member 206, the guide members 232, 272 and a central aperture 302 of the proximal wedge member 206 are illustrated. The central aperture 302 can be configured to receive an actuator shaft therethrough. When actuator shaft 210 is used in an embodiment, the central aperture 302 can be threaded to correspond to the threads 294 of the actuator shaft 210. In other embodiments, the actuator shaft can engage other portions of the wedge member 208 for causing expansion or contraction thereof.

Figure 19A:
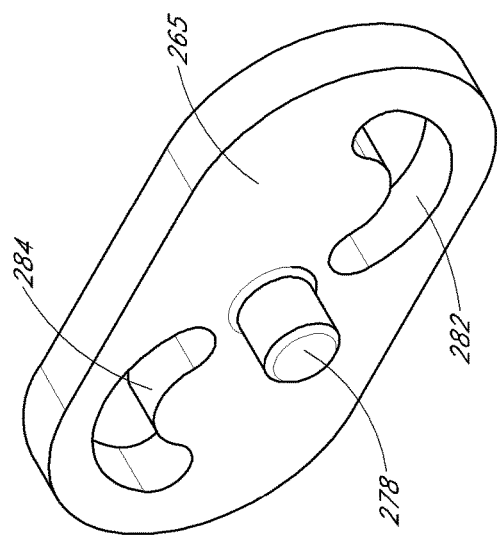
FIG. 19A illustrates a perspective view of a linkage of the intervertebral implant shown in FIG. 1.
Figure 19B:
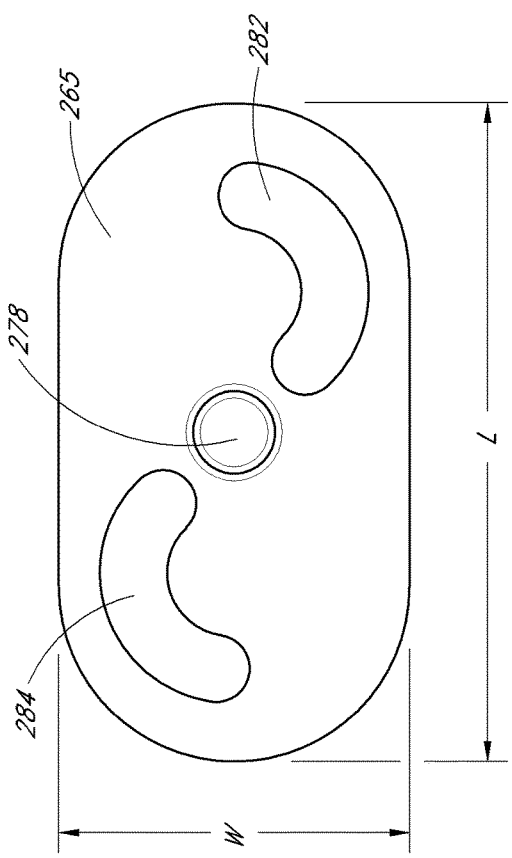
FIG. 19B illustrates a side view of the linkage illustrated in FIG. 19A.
Figure 19C:
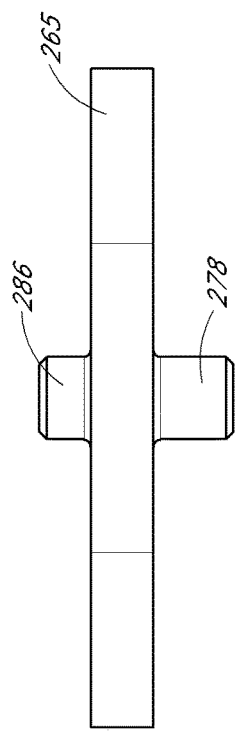
FIG. 19C illustrates a top view of the linkage illustrated in FIG. 19A.
Figure 21:
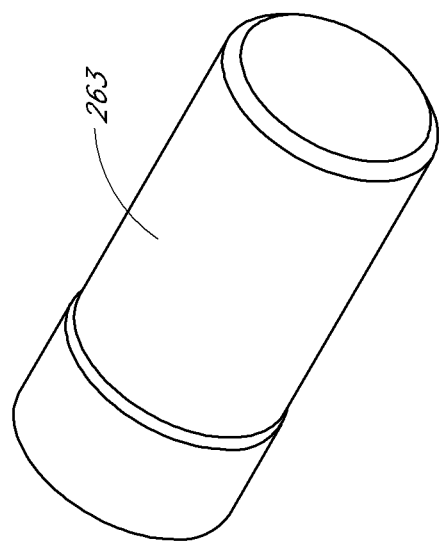
FIG. 21 is a perspective view of a short pin of the intervertebral implant shown in FIG. 1.
Figure 20:
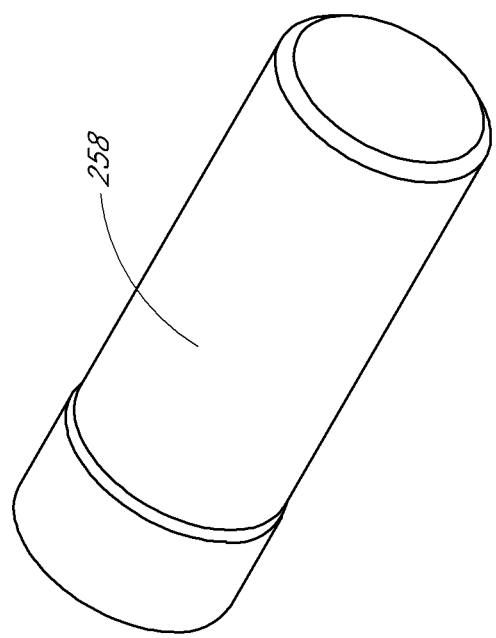
FIG. 20 is a perspective view of a long pin of the intervertebral implant shown in FIG. 1.

As shown in FIGS. 19A-19C, each linkage 254, 265 can have a width W and a length L. The length L can be substantially longer than the width W. In some embodiments, the length L can be at least two times the width W, at least three times the W, or otherwise. Each linkage 254, 265 can include one or more cam paths 282, 284 through which a long pin 258 (FIG. 20) or a short pin 263 (FIG. 21) can move. Each linkage can also include shaft portions 278, 286. The axis extending through the shaft portions 278, 286 can be substantially transverse to the longitudinal axis of the linkages 254, 265. Shaft portion 278 can be longer than shaft portion 286.

The linkages can be positioned such that the longer shaft portion 278 can engage the side portions 240, 242 of the upper and lower body portions 202, 204. For example, each of the side portions 240, 242 can include a receiving portion 293, 295 for receiving the longer shaft portion 278 when the implant 202 is in the unexpanded state. Each of the upper and lower body portions 202, 204 can also include internal receiving portions 297, 299 for receiving the shorter shaft portions 286 when the implant 200 is in the unexpanded state. The receiving portions can be slots, grooves, indentations, or other features capable of receiving the shaft portions 278, 286.

Figure 11:
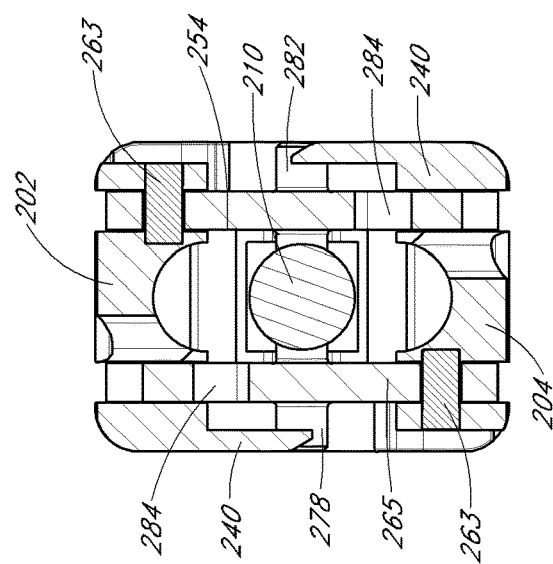
FIG. 11 is a front cross-sectional view of the intervertebral implant shown in FIG. 10 taken along lines 11-11.

The linkages 254, 265 can facilitate the alignment, interconnection, and stability of the upper and lower body portions 202, 204. As shown in FIG. 4, the long and short pins 258, 263 can connect the linkages 254, 265 to the upper and lower body portions 202, 204. The upper and lower body portions 202, 204 can each include apertures 290, 292 for receiving the pins 258, 263 (shown in FIGS. 12-13). For example, the long pin 258 can extend from the cam path 284 to the side portion aperture 290 disposed on the first side portion 240, and the short pin 263 can extend from the cam path 282 to the to the side portion aperture 292 disposed on the second side portion 242. FIG. 11 illustrates how the upper and lower body portions 202, 204 can connect to linkages 254, 265 via the pins 263. FIG. 11 illustrates a cross-section of FIG. 10 taken along line 11-11.

In addition, the linkages 254, 265 can act as motion limiting structures that limit the separation between the upper and lower body portions 202, 204. As the upper and lower side portions 202, 204 move apart, the pins 258, 263 move along their respective cam paths 282, 284 and force the linkages 254, 265 to rotate from the first configuration to the second configuration. In the first configuration, an axis extending across the width W of each linkage 254, 265 is substantially transverse to a longitudinal axis of the implant 200. In the second configuration, the axis extending across the width W of each linkage 254, 265 is nearly or substantially parallel to the longitudinal axis of the implant 200. The upper and lower body portions 202, 204 can only move apart so far as the linkages 254, 265 will permit. As such, the distance between the upper and lower body portions 202, 204 is limited by the distance between far ends of cam paths 282, 284.

Although not shown in the FIGS., the implant 200 can include additional linkages to provide further stability. Each of the additional linkages can connect to the upper and lower body portions 202, 204 as described above. For example, the additional linkages can be horizontally displaced from the first and second linkages 254, 265 described herein. In certain variants, the additional linkages can connect to the first and second linkages 254, 265 to permit further expansion of the upper and lower body portions 202, 204. For example, the upper and lower body portions 202, 204 can be separated by a distance equivalent to two linkages.

The specific dimensions of any of the embodiment disclosed herein can be readily varied depending upon the intended application, as will be apparent to those of skill in the art in view of the disclosure herein. Moreover, although the present inventions have been described in terms of certain preferred embodiments, other embodiments of the inventions including variations in the number of parts, dimensions, configuration and materials will be apparent to those of skill in the art in view of the disclosure herein. In addition, all features discussed in connection with any one embodiment herein can be readily adapted for use in other embodiments herein to form various combinations and sub-combinations. The use of different terms or reference numerals for similar features in different embodiments does not imply differences other than those which may be expressly set forth. Accordingly, the present inventions are intended to be described solely by reference to the appended claims, and not limited to the preferred embodiments disclosed herein.

What is claimed is:

1. An adjustable spinal fusion intervertebral implant comprising:
    upper and lower body portions each having proximal and distal surfaces at proximal and distal ends thereof, the proximal and distal surfaces of the upper and lower body portions generally facing each other;
    a proximal wedge member disposed at the proximal ends of the respective ones of the upper and lower body portions;
    a distal wedge member disposed at the distal ends of the respective ones of the upper and lower body portions;
    first and second linkages each connected to the upper and lower body portions, wherein the first and second linkages are rotatable with respect to the upper and lower body portions from a first configuration to a second configuration; and
    an actuator shaft received between the upper and lower body portions, the actuator shaft extending intermediate the distal and proximal wedge members, wherein rotation of the actuator shaft causes the distal and proximal wedge members to be drawn together such that longitudinal movement of the distal wedge member against the distal surfaces and the longitudinal movement of the proximal wedge member against the proximal surfaces causes separation of the upper and lower body portions.

2. The implant of claim 1, wherein the proximal surfaces of the respective ones of the upper and lower body portions each define a proximal slot therein, and distal surfaces of the respective ones of the upper and lower body portions each define a distal slot therein.

3. The implant of claim 2, wherein the slots of the proximal and distal surfaces of the upper and lower body portions are generally dove-tailed.

4. The implant of claim 2, wherein the proximal wedge member and the distal wedge member each comprise upper and lower guide members extending at least partially into the respective ones of the proximal and distal slots of the upper and lower body portions with at least a portion of the proximal wedge member and the distal wedge member contacting the proximal and distal surfaces of the upper and lower body portions.

5. The implant of claim 4, wherein the guide members of the proximal and distal wedge members are generally dove-tailed.

6. The implant of claim 1, wherein each of the upper and lower body portions further comprises a first side portion having an extending portion and a second side portion having a receiving portion, the first side portion of the upper body portion configured to mate with the second side portion of the lower body portion and the second side portion of the upper body portion configured to mate with the first side portion of the lower body portion.

7. The method of claim 6, wherein the first and second side portions of the upper body portion are configured to disengage from the first and second side portions of the lower body portion when the implant is in an expanded state.

8. The implant of claim 1, wherein the proximal and distal surfaces of the upper and lower body portions are sloped.

9. The implant of claim 1, wherein the upper and lower body portions comprise generally arcuate respective upper and lower exterior engagement surfaces.

10. The implant of claim 1, wherein the proximal wedge member comprises an anti-rotational element, the anti-rotational engagement being configured to be engaged by an implant tool for preventing rotation of the implant when the actuator shaft is rotated relative to the implant.

11. The implant of claim 10, wherein the anti-rotational element comprises a pair of apertures extending into the proximal wedge member.

12. The implant of claim 1, wherein the each of the first and second linkages include at least one cam path.

13. The implant of claim 12, wherein a pin extends from a respective one of at least one cam path to a respective one of the upper and lower body portions.

14. The implant of claim 12, wherein the at least one cam path is curved.

15. The implant of claim 12, further comprising pins that extend from respective ones of the at least one cam path to respective ones of the upper and lower body portions.

16. The implant of claim 1, wherein a length of the implant varies from about 45 mm to about 54 mm during the separation of the upper and lower body portions.

17. The implant of claim 1, wherein a length of the implant varies from about 21 mm to about 31 mm during the separation of the upper and lower body portions.

18. The implant of claim 1, wherein a height of the implant varies from about 6.5 mm to about 12 mm during the separation of the upper and lower body portions.

19. The implant of claim 1, wherein the upper and lower body portions are coated with a bio-active coating.

20. The implant of claim 19, wherein the bio-active coating is a hydroxyapatite coating.

21. A method of manufacturing the adjustable spinal fusion intervertebral implant of claim 1, the method comprising:
    extending the actuator shaft from the proximal wedge member to the distal wedge member, such that the actuator shaft is received between the upper and lower body portions, and the actuator shaft extends intermediate the proximal and distal wedge members, wherein the upper and lower body portions each have proximal and distal surfaces at proximal and distal ends thereof, the proximal and distal surfaces of the upper and lower body portions generally facing each other; and
    connecting the first and second linkages to each of the upper and lower body portions,
    wherein rotation of the actuator shaft causes the distal and proximal wedge members to be drawn together such that longitudinal movement of the distal wedge member against the distal surfaces and the longitudinal movement of the proximal wedge member against the proximal surfaces causes separation of the upper and lower body portions.

22. The method of claim 21, wherein extending the actuator shaft from the proximal wedge member to the distal wedge member comprises inserting the actuator shaft through a central aperture of the proximal wedge member and through a central aperture of the distal wedge member.

23. The method of claim 21, further comprising the step of extending upper and lower guide members of the proximal and distal wedge members at least partially into respective ones of proximal and distal slots of the upper and lower body portions so as to engage the first and second linkages with each of the upper and lower body portions.

24. The method of claim 21, further comprising engaging a first side portion of the upper body portion and a second side portion of the lower body portion, the first side portion having an extending portion and the second side portion having a receiving portion, the receiving portion configured to receive the extending portion.

25. The method of claim 21, further comprising the step of extending a pin from a cam path of one of the first and second linkages to one of the upper and lower body portions so as to engage the first and second linkages with each of the upper and lower body portions.

26. The method of claim 21, further comprising shot-peening the upper and lower body portions.

27. The method of claim 21, further comprising coating the upper and lower body portions with a bio-active coating.

28. The method of claim 27, wherein the bio-active coating is a hydroxyapatite coating.

29. The implant of claim 1, wherein the proximal and distal surfaces of the upper and lower body portions generally face each other along a direction, and the linkages have a height that is greater in the second configuration than in the first configuration, the height measured along the direction.

30. The implant of claim 29, configured such that moving the pins along the respective ones of the at least one cam path causes the first and second linkages to rotate from the first configuration to the second configuration.

* * * * *